US007642047B2

(12) United States Patent
Arumäe et al.

(10) Patent No.: US 7,642,047 B2
(45) Date of Patent: Jan. 5, 2010

(54) METHOD OF SCREENING CELL DEATH MODULATORS

(76) Inventors: Urmas Arumäe, Hanuripolku 6 B 34, FI-00420 Helsinki (FI); Li-Ying Yu, Rakentajantie 10 C 33, FI-00370 Helsinki (FI); Mart Saarma, Kulosaaren Puistotie 38 A 4, FI-00570 Helsinki (FI)

( * ) Notice: Subject to any disclaimer, the term of this patent is extended or adjusted under 35 U.S.C. 154(b) by 225 days.

(21) Appl. No.: 10/543,651

(22) PCT Filed: Jan. 29, 2004

(86) PCT No.: PCT/FI2004/000044

§ 371 (c)(1),
(2), (4) Date: Jul. 28, 2005

(87) PCT Pub. No.: WO2004/067767

PCT Pub. Date: Aug. 12, 2004

(65) Prior Publication Data

US 2006/0057721 A1    Mar. 16, 2006

(30) Foreign Application Priority Data

Jan. 29, 2003    (FI) ................................... 20030130

(51) Int. Cl.
*G01N 33/52* (2006.01)
*G01N 33/53* (2006.01)
(52) U.S. Cl. ............................. 435/4; 435/7.1; 435/325; 435/363; 435/366; 435/368
(58) Field of Classification Search ........................ None
See application file for complete search history.

(56) References Cited

U.S. PATENT DOCUMENTS

| 5,882,923 A | 3/1999 | Sariola et al. |
| 6,696,259 B1 | 2/2004 | Ibanez et al. |
| 6,713,247 B1 | 3/2004 | Sah et al. |

FOREIGN PATENT DOCUMENTS

| WO | WO-97/49798 A1 | 12/1997 |
| WO | WO-98/10058 A1 | 3/1998 |
| WO | WO-98/36057 A1 | 8/1998 |
| WO | WO-98/52591 A1 | 11/1998 |
| WO | WO-00/09669 A1 | 2/2000 |
| WO | WO-00/61172 A1 | 10/2000 |
| WO | WO-02/054066 A2 | 7/2002 |

OTHER PUBLICATIONS

Sepetov et al., Proc. Natl. Acad. Sci. 1995; 92: 5426-5430.*
Martins et al., JBC, 1997; 272: 7421-7430.*
Xu et al., Nucleic Acids Research, 1998; 26: 2034-2035.*
Ronald W. Oppenheim et al., Nature, vol. 373, Jan. 1995, pp. 344-346.
Yin Guo et al., The Journal of Biological Chemistry, vol. 277, No. 16, 2002, pp. 13430-13437.
Isabelle Martinou et al., The Journal of Cell Biology, vol. 144, No. 5, 1999, pp. 883-889.

* cited by examiner

*Primary Examiner*—Bridget E Bunner
*Assistant Examiner*—Christina Borgeest
(74) *Attorney, Agent, or Firm*—Birch, Stewart, Kolasch & Birch, LLP

(57) ABSTRACT

The invention provides methods and compositions for identifying agents which modulate cell death, indicated e.g. by the expression of caspase-2 and/or caspase-7, in GDNF family growth factor deprived neuronal or nonneuronal cells. The methods for identifying such agents find particular application in drug development.

11 Claims, 10 Drawing Sheets

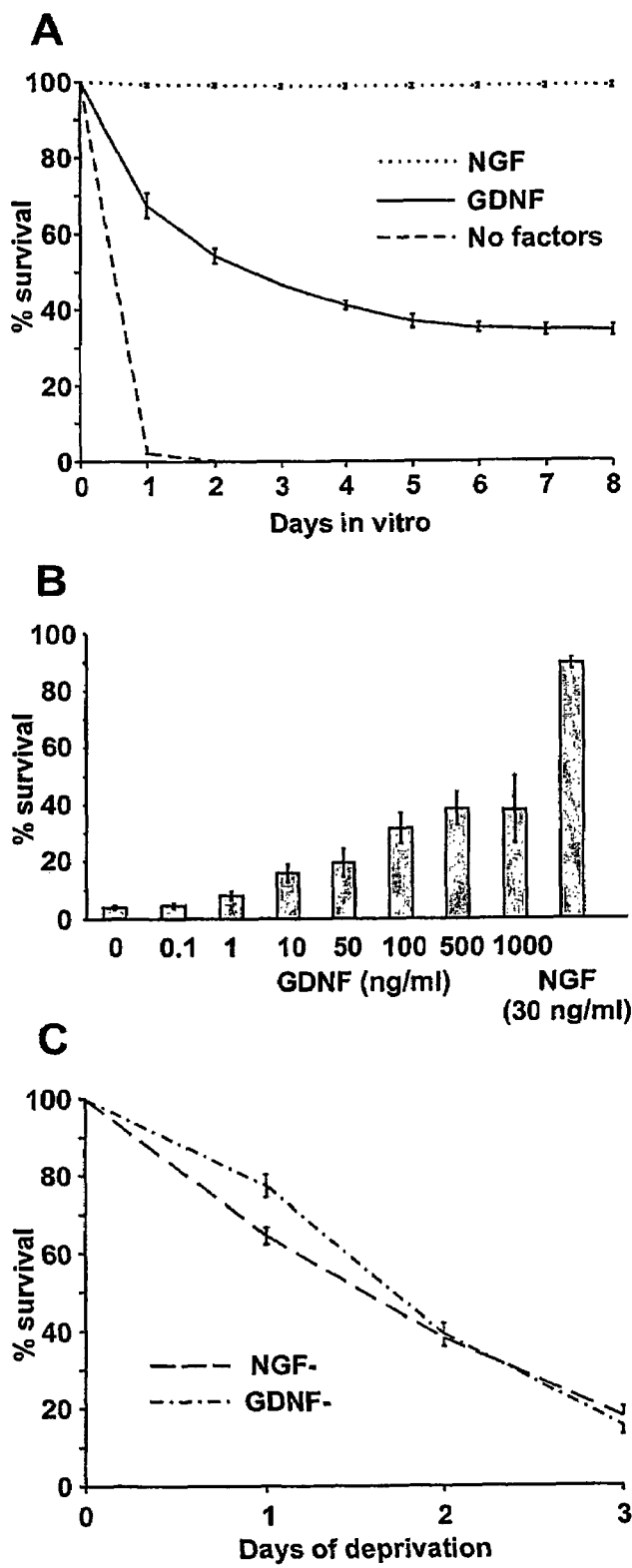
Figs. 1A, 1B, and 1C

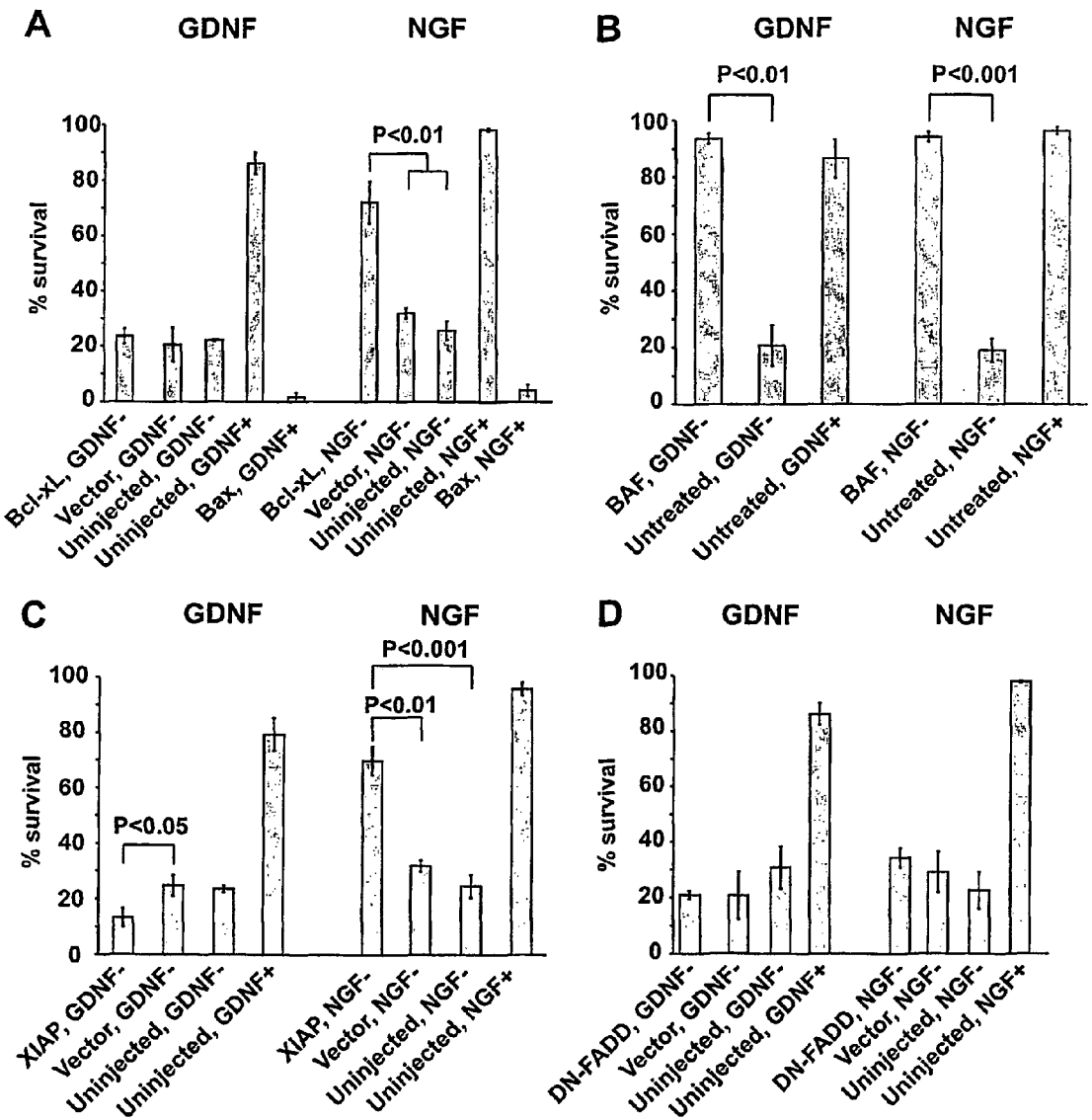
Fig. 5A, 5B, 5C, and 5D

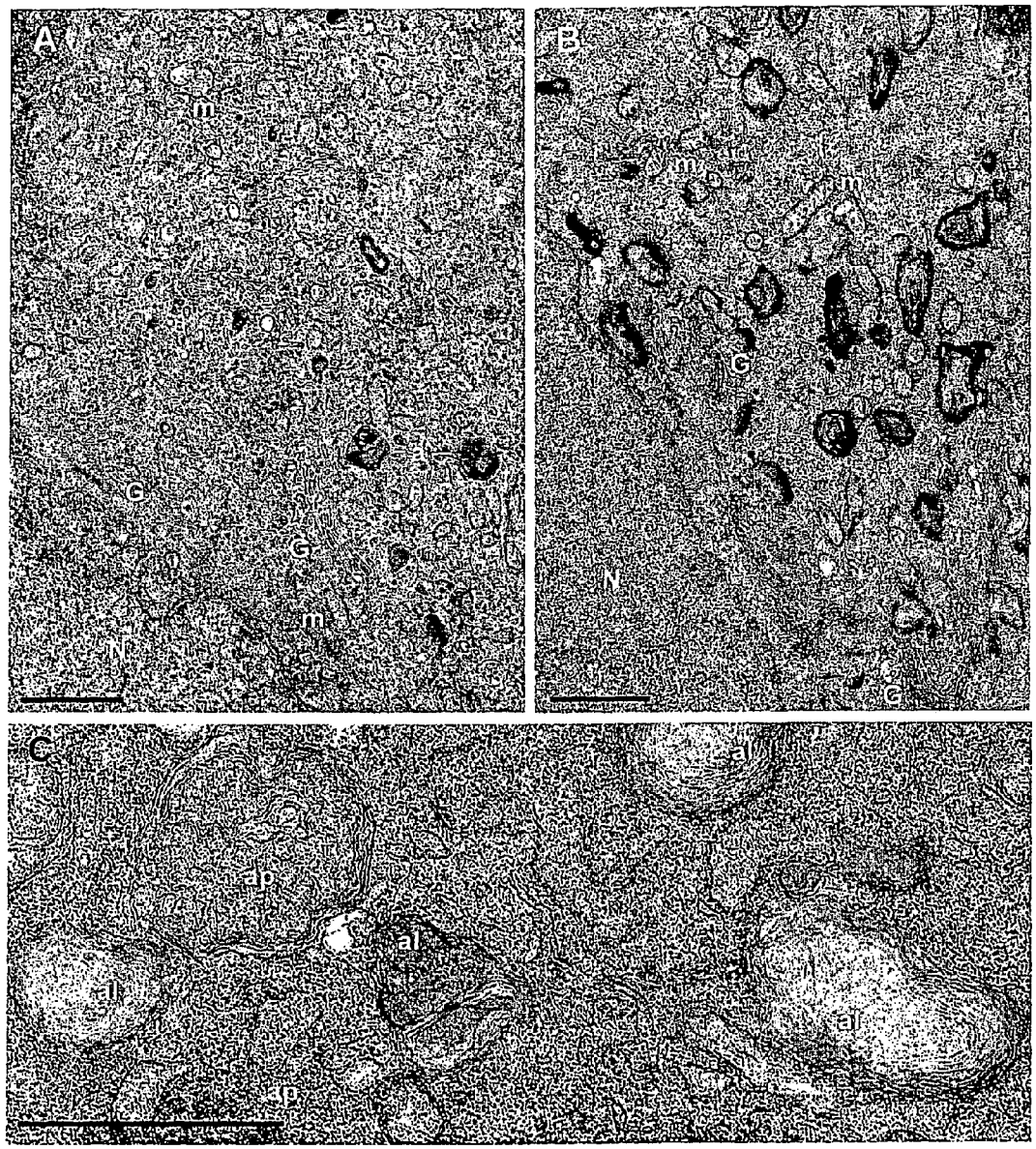
Fig. 7A, 7B, and 7C

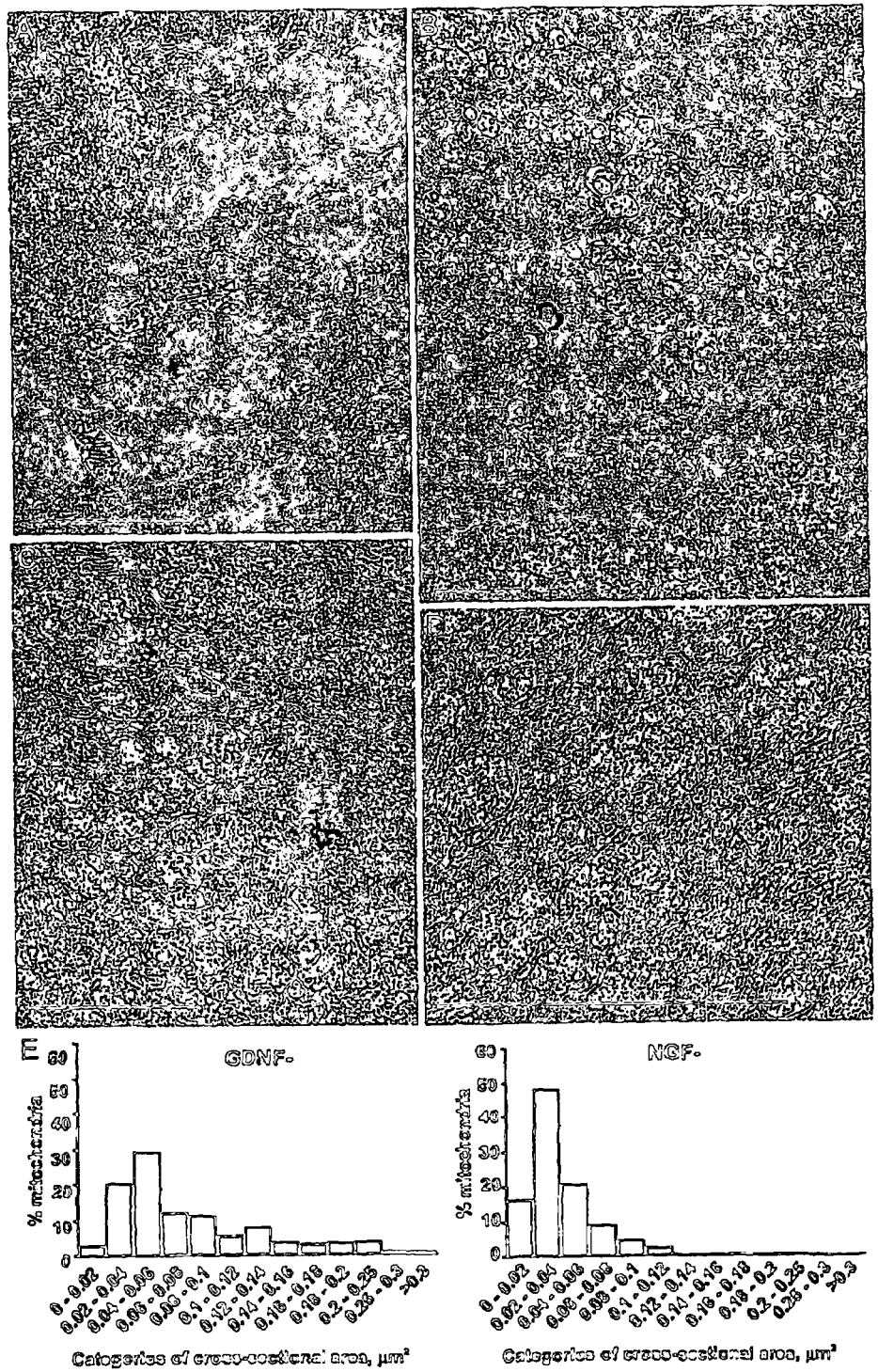
Fig 8A 8B 8C 8D and 8E

METHOD OF SCREENING CELL DEATH MODULATORS

The invention provides methods and compositions for identifying agents which prevent apoptosis, i.e. cell death, in growth factor deprived neuronal or nonneuronal cells.

BACKGROUND OF THE INVENTION

Programmed cell death is a process by which unwanted cells are intentionally removed, due to either physiological or pathological reasons. Morphological appearance of the dying cells and the death program (molecular and cellular death pathways) can differ remarkably between cell types and death stimuli (Clarke, 1990; Zimmermann et al., 2001; Leist and Jäättelä, 2001). Currently, two death pathways have been described in detail: the death receptor (extrinsic) and mitochondrial (intrinsic) pathway. The extrinsic pathway is activated by tumour necrosis factor receptor superfamily death receptor ligation (Vincenz, 2001). The death-inducing signaling complex, assembled directly at the death receptors, activates the initiator caspase-8 that in turn activates caspases-3, -6 and -7. Activation of the intrinsic death pathway leads to release of cytochrome c (but also other apoptotic molecules) from the mitochondrial intermembrane space to the cytosol. Cytosolic cytochrome c triggers formation of the apoptosome that activates the initiator caspase-9 followed by activation of caspase-3, -6 and -7. It was shown recently that caspase-2 is activated upstream of mitochondria and may participate in the activation of mitochondria-related death events (Guo et al., 2002; Lassus et al., 2002; Read et al., 2002).

Mitochondrial death pathway is triggered by different modes of cellular stress and in some cells by removal (deprivation) of survival (trophic) factors. The well-characterized example of such cells is the neonatal mouse or rat sympathetic neurons that critically depend on nerve growth factor (NGF) for survival. Withdrawal of NGF from the cultured sympathetic neurons leads to the following events. The protein levels and phosphorylation of transcription factor c-Jun are increased (Estus et al., 1994; Ham et al., 1995; Virdee et al., 1997; Eilers et al., 1998), pro-apoptotic protein Bax is translocated from the cytosol to the mitochondria Deckwerth et al., 1996; Putcha et al., 1999), cytochrome c is released from the mitochondria to the cytosol (Deshmukh and Johnson, 1998; Neame et al., 1998; Martinou et al., 1999) together with Smac/DIABLO, a protein that releases caspases from the Inhibitor of Apoptosis Proteins (Deshmukh et al., 2002). As a result, caspase-9, caspase-3 (Deshmukh et al., 2000; Deshmukh et al., 2002) but also caspase-2 (Troy et al., 2001) are activated. All these events are critically required for the NGF deprivation-induced death. The neurons then exhibit classical features of apoptosis, including condensation of chromatin, cleavage of DNA but also increased autophagy (Martin et al., 1988; Pittman et al., 1993; Edwards and Tolkovsky, 1994; Xue et al., 1999) and die finally in the culture by secondary necrosis.

In addition to these two, several other death pathways exist (Clarke, 1990; Leist and Jäättelä, 2001) but these remain largely unknown. Cells in which the intrinsic apoptotic pathway is blocked can still be induced to die, both in vitro and in vivo, often with nonapoptotic ultrastructure (Yaginuma et al., 2001; Oppenheim et al., 2001; Zaidi et al., 2001; Marsden et al., 2002). Recently, novel death pathways have been proposed for the dependence receptors that trigger death by a novel mechanism, when not occupied with their cognate ligands, whereas ligation of the receptors blocks death (Rabizadeh et al., 1993; Ellerby et al., 1999; Bordeaux et al., 2000; Llambi et al., 2001; Thibert et al., 2003). In the case of the Deleted in Colorectal Cancer receptor, this mechanism includes direct interaction of caspases with the receptor and does not require the death receptors or mitochondrial pathways. Certainly further death pathways exist.

NGF is currently the best-characterized neurotrophic factor. Although many more neurotrophic factors are known that promote survival of different types of neurons (Huang and Reichardt, 2001), the death pathways activated by their withdrawal are virtually unstudied. Glial cell line-derived neurotrophic factor (GDNF) (Airaksinen and Saarma, 2002) is a neurotrophic factor that promotes survival of several neuronal populations, including neonatal rat sympathetic neurons (Kotzbauer et al., 1996). NGF and GDNF signal via different receptor systems: TrkA/p75 for NGF and Ret/GFRα1 complex for GDNF. We compared the death programs triggered in the same cell type (sympathetic neurons) by removal of two different neurotrophic factors (NGF or GDNF). Surprisingly we found that the death pathways activated in these two cases differ considerably.

SUMMARY OF THE INVENTION

The invention provides methods and compositions for identifying agents which modulate cell death, indicated e.g. by the expression of caspase-2 and/or caspase-7, in GDNF family growth factor deprived neuronal or nonneuronal cells. The methods for identifying such agents find particular application in commercial drug screens.

In particular, the invention provides a method of screening cell death modulators of neuronal or nonneuronal cells in a GDNF family growth factor dependent cell culture system comprising the steps of removing the GDNF family growth factor from the culture system, introducing a candidate modulator agent into the culture system, and determining the activity of caspase-2 and/or caspase-7.

BRIEF DESCRIPTION OF THE DRAWINGS

FIGS. 1A, 1B, and 1C. Culture conditions for GDNF-responsive newborn rat sympathetic neurons from the superior cervical ganglion. (1A) Newly isolated neurons were grown with GDNF (100 ng/ml), NGF (30 ng/ml) or without neurotrophic factors for eight days. The living neurons were counted daily and expressed as percent of initial neurons, counted two hours after plating. The mean±standard error of the mean of three independent cultures is shown for each data point. (1B) Newly isolated neurons were maintained with different doses of GDNF for six days. The living neurons were counted daily and expressed as percent of initial neurons, counted two hours after plating. For comparison, survival with NGF (30 ng/ml) is also shown. The mean±standard error of the mean of three independent cultures is shown for each data point. (1C) Neurons were first maintained with GDNF (100 ng/ml) or NGF (30 ng/ml) for six days. Neurotrophic factors were then removed (0-day of deprivation) and the neurons were grown further without them. Living neurons were counted daily and expressed as percent of initial neurons counted immediately after factor deprivation. The mean±standard error of the mean of six independent cultures is shown for each data point.

FIGS. 5A, 5B, 5C, and 5D. Involvement of proteins of the apoptotic machinery in the death of GDNF- or NGF-deprived sympathetic neurons. (5A) Overexpressed Bcl-$x_L$ rescues NGF-deprived but not GDNF-deprived neurons, whereas overexpressed Bax kills both types of neurons. (5B) Broad-range caspase inhibitor BAF (50 μg/ml) protects both GDNF- and NGF-deprived neurons. (5C) Overexpressed XIAP protects NGF-deprived but not GDNF-deprived neurons. (5D) Overexpressed dominant negative FADD (DN FADD) does protect neither GDNF- nor NGF-deprived neurons. In (5A-D), the living neurons were counted 72 h after treatment and neurotrophic factor deprivation, and expressed as percent of initial neurons. The mean±standard error of the mean of three independent cultures is shown for each data point. Data of Bcl-$x_L$-(5A), XIAP- (5C) or DN FADD-injected (5D) neurons were compared to respective vector-injected or untreated neurotrophic factor-deprived controls by one-way ANOVA and post hoc Tukey's honestly significant difference test.

Data of BAF-treated neurons (5B) were compared to untreated controls by Student's t test.

Figure 6A:
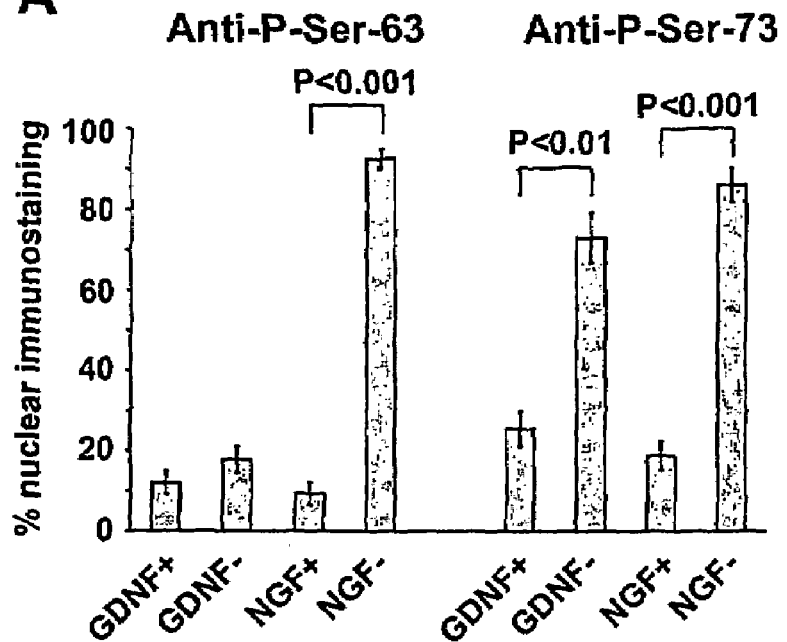
Figure 6B:
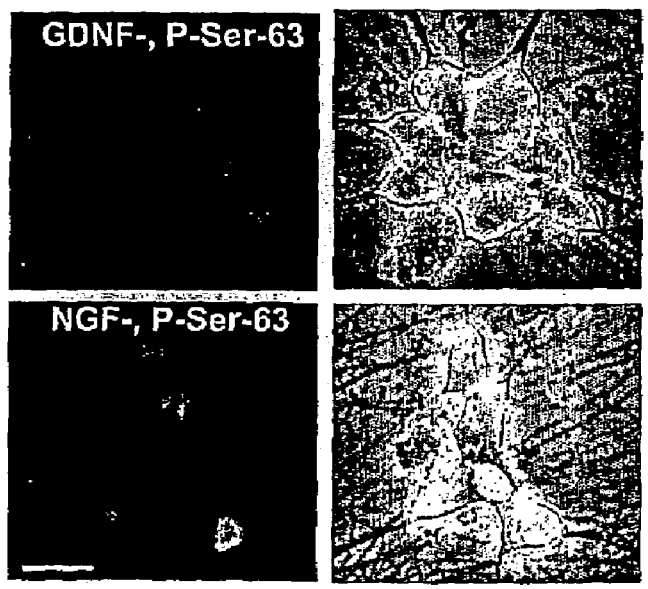

FIGS. 6A and 6B. Activation of MLK and c-Jun is required for the death of GDNF-deprived sympathetic neurons. (6A) Quantitation of neurons with strong nuclear immunostaining for phosphorylated c-Jun, expressed as percent of all neurons. Neurons were deprived of neurotrophic factors in the presence of caspase inhibitor BAF for 48 hours and immunostained with antibodies to phosphorylated serines 63 or 73 of c-Jun. Control-neurons maintained with GDNF or NGF were stained as well. The mean±standard error of the mean of four (for P-Ser-63) or three (for P-Ser-73) independent cultures is shown for each data point. Neurotrophic factor-maintained and -deprived groups were compared by Student's t test. (6B) Typical examples of weak (GDNF-deprived neurons) or strong (NGF-deprived neurons) nuclear immunostaining. Corresponding phase contrast images are shown on the right column. Levels of the fluorescent images were equally enhanced with Adobe Photoshop software. Scale bar, 10 μm.

FIGS. 7A, 7B and 7C. Autophagy is greatly enhanced in GDNF-deprived sympathetic neurons. (7A) Ultrastructure of a typical GDNF-maintained neuron with normal mitochondria (m), Golgi complex (G), and two dark autolysosomes (a) that are sparse in these neurons. (7B) Typical GDNF-deprived neuron from sister dish showing largely increased number of autolysosomes, but normal mitochondria and Golgi complex. N: nucleus. (7C). A detail from another GDNF-deprived neuron with double-membraned autophagosomes (ap) and single-membraned autolysosomes (al) containing swirled packages of undigested membranes. Scale bar: 1 μm.

FIGS. 8A, 8B, 8C, and 8E. Mitochondria of NGF-deprived, but not GDNF-deprived, sympathetic neurons are structurally changed. (8A) Typical view of a GDNF-deprived neuron with numerous dark autophagic profiles and several nonclustered elongated mitochondria with normal cristae. (8B) A NGF-deprived neuron with several dark autolysosomes and large number of round clustered mitochondria with changed cristae. N: nucleus. (8C) Higher magnification of the mitochondrial cluster with vesicular cristae and one membrane in a NGF-deprived neuron. (8D) Mitochondria whose cristae and inner membrane are altered to different extent in a NGF-deprived neuron. Scale bar: 1 μm. (8E) Distribution of mitochondrial profiles from the sections of GDNF-deprived (n=201) and NGF-deprived (n=317) neurons according to their cross-sectional areas. Size categories are shown as percent of all mitochondrial profiles.

Figure 9:
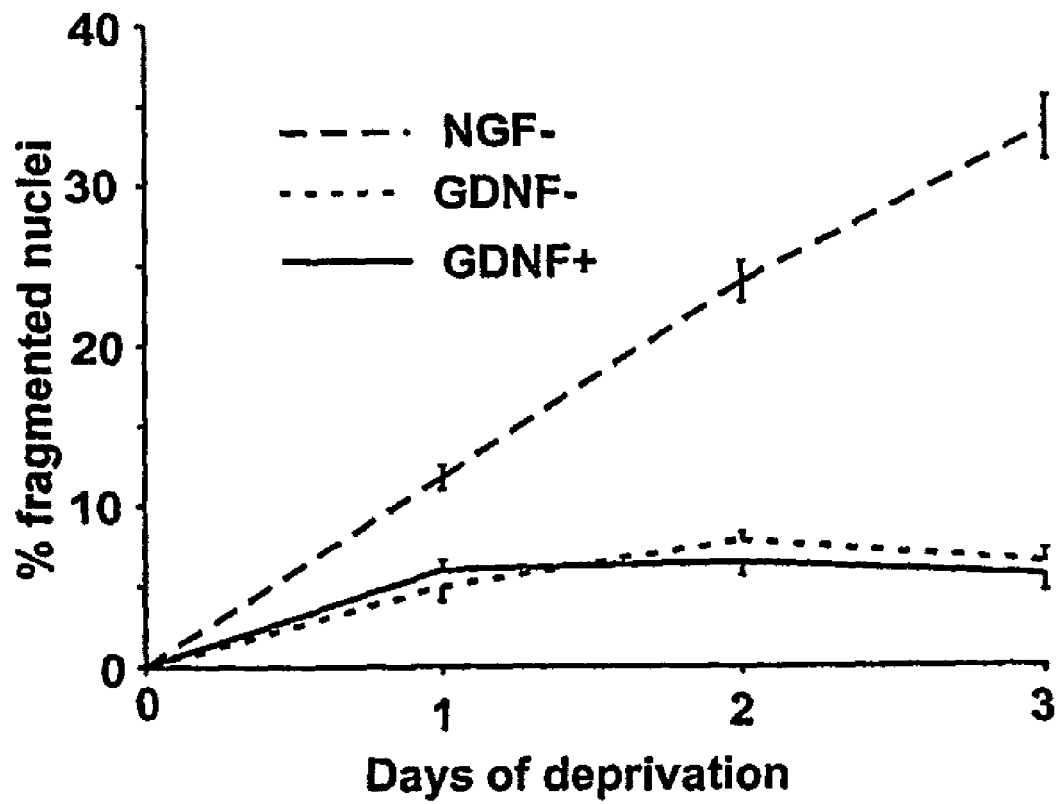

FIG. 9. GDNF deprivation does not induce chromatin condensation and nuclear fragmentation in the sympathetic neurons. Six DIV neurons were deprived of or maintained with GDNF or NGF. The cultures were fixed daily and stained with Hoechst 33258. The neurons with fragmented nuclei and condensed chromatin were counted and expressed as percent of all neurons. The mean±standard error of the mean of four independent experiments is shown for each data point.

DETAILED DESCRIPTION OF THE INVENTION

Growth factors referred in this invention comprise growth factors which posses activities for neuronal or nonneuronal cells. Growth factors useful in this invention comprise GDNF family members, different FGFs, IGFs, TGF-betas, EGFs, CNTF, LIF, NGF, BDNF, NT-4, NT-4 and AL-1.

GDNF family members comprise GDNF (glial cell line-derived neurotrophic factor), NRTN (neurturin), ARTN (artemin) and PSPN (persephin).

As used herein, the term "neurons" or "neuronal cells" are intended to include the neurons of the central nervous system and peripheral nervous system. Preferred neurons are mammalian neurons, more preferably human neurons.

As used herein, the term "nonneuronal" are intended to include cells as astrocytes, oligodendrocytes, kidney cells, chromaffin cells, T-cells, i.e. cells not encompassed in term "neuron".

We describe here that removal of GDNF from the cultured sympathetic neurons triggers a novel nonmitochondrial caspase-dependent death pathway. We have discovered that in GDNF-deprived apoptotic neurons, at least caspase-2 and caspase-7 are activated. Thus, the present invention provides a method, which can be used in screening cell death modulators of neuronal or nonneuronal cells in a GDNF family growth factor-dependent cell culture system, wherein candidate modulators are introduced into the system and effective modulators are identified by determining the activity of caspase-2 and/or caspase-7 after GDNF deprivation. Active modulators discovered by the method may be used in drug development.

Cell Culture Methods for Identifying Caspase-2 and/or Caspase-7 Modulators

In one embodiment, the invention contemplates in vitro methods for culturing neuronal or nonneuronal cells under conditions where the caspase-2 and/or caspase-7 modulating agent are used to prevent cell death and can include methods for detecting the presence and amount of modulation of caspase-2 and/or caspase-7 activity.

Appropriate cells are prepared for identification of caspase-2 and/or caspase-7 modulating agents in a growth factor deprivation assay. For example, a preparation of superior cervical ganglion neurons is disclosed in the Experimental Section. Another appropriate cells are dorsal root ganglion cells, nodose ganglion neurons, spinal motoneurons, midbrain dopaminergic neurons, central noradrenergic neurons and enteric neurons. The nonneuronal cells for the identification of caspase-2 and/or caspase-7 modulating agents are chromaffin cells of the adrenal medulla, cells of embryonic kidney, differentiating spermatogonia or T-cells of the thyroid gland.

Before beginning the assay, the cells may be resuspended, added to substrate-coated dishes, and placed under predetermined assay conditions for a preselected period of time. After the attachment and growth period, the dishes may be rinsed to remove unbound cells, fixed, and viewed e.g., by phase contrast microscopy.

Preferably, a plurality of cells are analysed for each substrate. Cells are then "judged" based on predetermined criteria. For example, cells may be considered apoptotic if they show typical signs of apoptotic death. The percent of cells that are dying is preferably determined. A particularly preferred cell death assay method is disclosed in the Experimental Section.

In one embodiment, the invention provides a method of screening cell death modulators of neuronal or nonneuronal cells in a GDNF family growth factor dependent cell culture system comprising the steps of (1) removing the GDNF family growth factor from the culture system; (2) introducing a candidate modulator agent into the culture system; and (3) determining the activity of caspase-2 and/or caspase-7. Steps 1 and 2 can be performed in any order. Preferably, step 2 is performed before step 1, more preferably, step 1 and 2 are performed simultaneously. Step 3 can be performed several times during the screening procedure.

The invention also discloses compositions comprising agents exhibiting a caspase-2 and/or caspase-7 modulating activity in substantially pure form.

In Vivo Methods for Prevention of Cell Death

The various caspase-2 and/or caspase-7 activity modulating agents are also useful in a variety of therapeutic applications as described herein.

The present therapeutic methods are useful in treating growth factor deprived neurons or nonneuronal cells associated with physical or surgical trauma, infarction, toxin exposure, degenerative disease, malignant disease that affects peripheral or central neurons, or in surgical or transplantation methods in which neuronal cells from brain, spinal cord or dorsal root ganglia are exposed to reduced levels of growth factors and require cell death preventive therapy. Such diseases further include but are not limited to CNS lesions, gliosis, Parkinson's disease, Alzheimer's disease, neuronal degeneration, enteric diseases, kidney disease, immunogical diseases, diseases of chromaffin cells and the like.

In treating growth factor deprivation, contacting a therapeutic composition of this invention with the deprived cells soon after injury is particularly important for accelerating the rate and extent of recovery.

Thus the invention contemplates a method of preventing cell death in growth factor deprivation in a subject, or in selected tissues thereof, comprising administering to the subject or the tissue a physiologically tolerable composition containing a therapeutically effective amount of an agent of the present invention.

In preferred methods, the subject is a human patient.

In one embodiment, a cell undergoing growth factor deprivation may be repaired by administering a caspase-2 and/or caspase-7 modulating agent.

In a related embodiment, a caspase-2 and/or caspase-7 modulating agent is administered orally in a pharmaceutically accepted formula. The target cell may reside in culture or in situ, i.e. within the natural host. For in situ applications, the compositions are added to a retained physiological fluid such as blood or synovial fluid. For CNS administration, a variety of techniques are available for promoting transfer of the therapeutic agent across the blood brain barrier including disruption by surgery or injection, drugs which transiently open adhesion contact between CNS vasculature endothelial cells, and compounds which facilitate translocation through such cells. A caspase-2 and/or caspase-7 modulating agent may also be amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. Generally, the amount administered will be empirically determined, typically in the range of about 10 to 1000 micrograms/kg of the recipient and the concentration will generally be in the range of about 50 to 500 micrograms/ml in the dose administered. Other additives may be included, such as stabilizers, bactericides, etc. will be present in conventional amounts.

Therapeutic compositions of the present invention may include a physiologically tolerable carrier together with at least one caspase-2 and/or caspase-7 modulating agent of this invention as described herein, dispersed therein as an active ingredient. In a preferred embodiment, the therapeutic composition is not immunogenic when administered to a human patient for therapeutic purposes.

For the sake of simplicity, the active agent of the therapeutic compositions described herein shall be referred to as a "caspase-2 and/or caspase-7 modulating agent". It should be appreciated that this term is intended to encompass a variety of agents including such small molecules which include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Any of a variety of mammalian cells or neuronal cells can be treated by the present method of treatment in vivo, including neuronal cells from brain, CNS, peripheral nerves and the like. In a preferred embodiment these cells are superior cervical ganglion cells. In another preferred embodiment these cells are dorsal root ganglion cells, nodose ganglion neurons, spinal motoneurons, midbrain dopaminergic neurons, central noradrenergic neurons and enteric neurons. In still another preferred embodiment these cells comprise chromaffin cells of the adrenal medulla, cells of embryonic kidney, differentiating spermatogonia or T-cells of the thyroid gland.

In addition, the cells can be from any of a variety of mammalian species, including human, mouse, chicken, and any other mammalian species, including the agricultural stock and non-domesticated mammals.

Therapy

The present invention also encompasses agents which modulate caspase-2 and/or caspase-7 expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Screening Assays

The subject methods include screens for agents which modulate caspase-2 and/or caspase-7 interactions and methods for modulating these interactions. Caspase-2 and/or caspase-7 activation is found to regulate cell death, more particularly growth factor deprivation dependent cell death. Accordingly, the invention provides methods for modulating targeted cell function comprising the step of modulating caspase-2 and/or caspase-7 activation by contacting the cell with a modulator agent of a caspase-2 and/or caspase-7 activation.

In another aspect, the invention provides methods of screening for agents which modulate caspase-2 and caspase-7 interactions. These methods generally involve forming a mixture of a caspase-2 and caspase-7-expressing cell and a candidate agent, and determining the effect of the agent on the amount of caspase-2 and/or caspase-7 expressed by the cell. The methods are amenable to automated, cost-effective high throughput screening of chemical libraries for lead compounds. Identified reagents find use in the pharmaceutical industries for animal and human trials; for example, the reagents may be derivatized and rescreened in vitro and in vivo assays to optimize activity and minimize toxicity for pharmaceutical development. More specifically, neuronal cell based growth factor deprivation assay is described in detail in the experimental section below.

The invention further provides methods (also referred to herein as "screening assays") for identifying modulators, i.e., candidate or test compounds or agents (e.g., peptides, peptidomimetics, peptoids, small molecules or other drugs) which bind to caspase-2 and/or caspase-7 proteins, have a stimulatory or inhibitory effect on, for example, caspase-2 and/or caspase-7 expression or caspase-2 and/or caspase-7 activity, or have a stimulatory or inhibitory effect on, for example, the expression or activity of an caspase-2 and/or caspase-7 substrate. Compounds thus identified can be used to modulate the activity of caspase-2 and/or caspase-7 in a therapeutic protocol, to elaborate the biological function of the caspase-2 and/or caspase-7, or to identify compounds that disrupt normal caspase-2 and/or caspase-7 interactions. The preferred caspase-2 and caspase-7 used in this embodiment are the human caspase-2 and caspase-7 of the present invention.

In one embodiment, the invention provides assays for screening candidate or test compounds which are substrates of an caspase-2 and/or caspase-7 protein or polypeptide or biologically active portion thereof. In another embodiment the invention provides assays for screening candidate or test compounds which bind to or modulate the activity of an caspase-2 and/or caspase-7 protein or polypeptide or biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. J. Med. Chem. 1994, 37: 2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) Anticancer Drug Des. 12:145).

In one embodiment, an assay is a cell-based assay in which a cell which undergoes growth factor deprivation is contacted with a test compound and the ability of the test compound to modulate caspase-2 and/or caspase-7 activity is determined. Determining the ability of the test compound to modulate caspase-2 and/or caspase-7 activity can be accomplished by monitoring, for example, cell death, cell growth, cell attachment, neurite outgrowth, and cell chemotaxis. The cell, for example, can be of mammalian origin, e.g., a neuronal cell. In preferred embodiment, caspase-2 and/or caspase-7 is expressed in neuronal cells and the ability of the test compound to modulate caspase-2 and/or caspase-7 activity is accomplished by monitoring cell death or alternatively, by monitoring caspase-2 and caspase-7 activation with Western blot, immunohistochemical staining using anti caspase-2 or caspase-7 antibodies, or fluorometric assays described in experimental section.

Determining the ability of the caspase-2 and/or caspase-7 or a biologically active fragment thereof, to bind to or interact with an agent can be accomplished by one of the methods described above for determining direct binding. In a preferred embodiment, determining the ability of the caspase-2 and/or caspase-7 protein to bind to or interact with an agent can be accomplished by determining the activity of the caspase-2 and/or caspase-7. For example, the activity of the caspase-2 and/or caspase-7 can be determined by detecting catalytic/enzymatic activity of the caspase-2 and/or caspase-7 upon an appropriate substrate (for example a fluorometric assay using caspase-2 or caspase-7 specific substrates), detecting the induction of a reporter gene (recombinant caspase-2 and/or caspase-7 gene products labelled with detectable marker), or detecting a target-regulated cellular response (i.e., cell attachment, adhesion, growth, death or migration).

In yet another embodiment, an assay of the present invention is a cell-free assay in which an caspase-2 and/or caspase-7 protein or biologically active portion thereof is contacted with a test compound and the ability of the test compound to bind to the caspase-2 and/or caspase-7 protein or biologically active portion thereof is determined. Preferred biologically active portions of the caspase-2 and/or caspase-7 proteins to be used in assays of the present invention include fragments which posses sites of their enzymatic activity.

The caspase-2 and/or caspase-7 proteins of the invention can, in vivo, interact with one or more cellular macromolecules, such as proteins. For the purposes of this discussion, such cellular macromolecules are referred to herein as "binding partners." Compounds that disrupt such interactions can be useful in regulating the activity of the caspase-2 and/or caspase-7. Such compounds can include, but are not limited to molecules such as peptides and small molecules. Towards this purpose, in an alternative embodiment, the invention provides methods for determining the ability of the test compound to modulate the activity of a caspase-2 and/or caspase-7 protein through modulation of the activity of a upstream effector molecule of an caspase-2 and/or caspase-7. For example, the activity of the effector molecule on an caspase-2 and/or caspase-7 can be determined, or the binding of the effector to caspase-2 and/or caspase-7 can be determined as previously described.

Assays for the Detection of the Ability of a Test Compound to Modulate Expression of Caspase-2 and/or Caspase-7

In another embodiment, modulators of caspase-2 and/or caspase-7 expression are identified in a method wherein a cell is contacted with a candidate compound/agent and the expression of caspase-2 and/or caspase-7 mRNA or protein in the cell is determined. The level of expression of caspase-2 and/or caspase-7 mRNA or protein in the presence of the candidate compound is compared to the level of expression of caspase-2 and/or caspase-7 mRNA or protein in the absence of the candidate compound. The candidate compound can then be identified as a modulator of caspase-2 and/or caspase-7 expression based on this comparison. For example, when expression of caspase-2 and/or caspase-7 mRNA or protein is greater (statistically significantly greater) in the presence of the candidate compound than in its absence, the candidate compound is identified as a stimulator of caspase-2 and/or caspase-7 mRNA or protein expression. Alternatively, when expression of caspase-2 and/or caspase-7 mRNA or protein is less (statistically significantly less) in the presence of the candidate compound than in its absence, the candidate compound is identified as an inhibitor of caspase-2 and/or caspase-7 mRNA or protein expression. The level of caspase-2 and/or caspase-7 mRNA or protein expression in the cells can be determined by methods described herein for detecting caspase-2 and/or caspase-7 mRNA or protein.

Combination Assays

In another aspect, the invention pertains to a combination of two or more of the assays described herein. For example, a modulating agent can be identified using a cell-based or a cell free assay, and the ability of the agent to modulate the activity of an caspase-2 and/or caspase-7 protein can be confirmed in vivo, e.g., in an animal such as an animal model for CNS disorders, or for cellular transformation and/or neuronal death.

This invention farther pertains to novel agents identified by the above-described screening assays. Accordingly, it is within the scope of this invention to further use an agent identified as described herein in an appropriate animal model. For example, an agent identified as described herein (e.g., an caspase-2 and/or caspase-7 modulating agent, an antisense caspase-2 and/or caspase-7 nucleic acid molecule, an caspase-2 and/or caspase-7-specific antibody, or an caspase-2 and/or caspase-7-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The choice of assay format will be based primarily on the nature and type of sensitivity/resistance protein being assayed. A skilled artisan can readily adapt protein activity assays for use in the present invention with the genes identified herein.

For example, activation of caspases (proteolytic cleavage of the inactive pro-caspase into smaller subunits) can be detected by Western blotting. A 48 kD precursor of caspase-2 is cleaved into p16, p18 and p12, and a 33 kD precursor of caspase-7 is cleaved into P12 and p19. The antibodies are commercially available (e.g. Santa Cruz Biotechnology). Caspase activation can also be detected by fluorometrically by FRET-technology (see below).

In a preferred embodiment of the invention, the activation of the GDNF-deprived cell death pathway in the cells can be checked by the activation of caspase-2 and caspase-7 in the conditions where caspase-3 (but also caspase-9 and caspase-8), as well as Bax, are not activated. Caspase-2 is often activated also in the "classical" apoptosis but always together with caspase-3 (and either caspase-9 or caspase-8). In the death pathway activated by GDNF deprivation, caspase-2 is activated without the activation of caspase-3, -9, or -8. Bax protein, that is essential in "classical" apoptosis, is also not activated in the death pathway triggered by GDNF deprivation.

The activation of specific caspases can be checked by fluorescence resonance electron transfer (FRET)-technique using caspase-specific probes (Takemoto K, Nagai T, Miyawaki A, Miura M. Spatio-temporal activation of caspase revealed by indicator that is insensitive to environmental effects. J. Cell Biol. 2003; 160(2): 23543). In these probes, cyan fluorescent protein is linked to yellow fluorescent protein by a peptide containing a cleavage site for the particular caspase. When activated, the caspase cleaves the probe that changes the fluorescence emission from cyan to yellow. The plasmids containing FRET probes can be transfected into the cells by different cell type-specific means. Fluorescence of the transfected cells can be monitored in dying cells by inverted microscope equipped with the fluorescence filters for cyan and yellow fluorescent proteins.

Thus, the present invention is also related to fluorescence resonance energy transfer (FRET) which refers to distance-dependent interaction between the electronically excited states of two dye molecules in which excitation energy is transferred from a donor molecule to an acceptor molecule without emission of a photon. Primary conditions for FRET are: (i) donor (source) and acceptor (target) molecules must be in close proximity (typically 10-100 Å), (ii) the absorption spectrum of the acceptor must overlap the fluorescence emission spectrum of the donor. Probes labeled with such energy transfer coupled dyes are described, e.g., in U.S. Pat. No. 6,028,190. Any pair or pool of dyes capable of FRET can be used in the present invention.

Furthermore, the activation of Bax in the dying cells can be checked by cell-permeable Bax-inhibiting peptides to Ku70, a protein that normally binds to Bax and keeps it inactive in healthy cells (Sawada M, Hayes P, Matsuyama S. Cytoprotective membrane-permeable peptides designed from the Bax-binding domain of Ku70. Nat Cell Biol. 2003 April; 5(4): 352-7). These peptides block the apoptotic death where Bax is involved, but do not block the death induced by GDNF deprivation.

The publications and other materials used herein to illuminate the background of the invention, and in particular, to provide additional details with respect to its practice, are incorporated herein by reference.

The invention will be described in more detail in the experimental section. However, it will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

EXPERIMENTAL SECTION

Materials and Methods

Culture of Sympathetic Neurons and the Survival Assays

Culture of the superior cervical ganglion (SCG) neurons was performed as published (Hamner et al., 2001; Sun et al., 2001; Lindahl et al., 2001). Briefly, the neurons of postnatal day-1-2 Han/Wi strain rats were grown six days in vitro on polyornithine-laminin-coated dishes or glass coverslips with 100 ng/ml of human GDNF (PeproTech) or 30 ng/ml of 2.5 S mouse NGF (Promega). 4-5 times more neurons were initially plated for GDNF-experiments compared to NGF-controls, so that by the day of neurotrophic factor deprivation, the number of neurons in both groups was similar. To reduce the number of nonneuronal cells, 1 $\mu$M cytosine arabinoside (Sigma-Aldrich) was always included next day after plating, but was not added to factor-deprived neurons. To deprive GDNF, the cultures were washed gently three times with GDNF-free culture medium. To remove NGF, the cultures were washed once with NGF-free medium and function-blocking anti-NGF antibodies (Roche) were added. The compounds of interest were added and initial neurons were counted immediately after neurotrophic factor deprivation. Living neurons were counted daily by a "blind" experimenter not aware of the identity of experimental groups. The following compounds were assayed: broad-range caspase inhibitor boc-aspartyl(OMe)-fluoromethylketone. (BAF) (Enzyme Systems Products) at 50 $\mu$M; pCPT-cAMP (Sigma-Aldrich) at 500 nM, V5 and I5 peptides at 200 $\mu$M. When the compounds were dissolved in DMSO, the same amount of DMSO was always added to the control cultures.

Microinjections

The neurons were pressure-microinjected with expression plasmids (50 ng/$\mu$l) encoding the proteins of interest together with enhanced GFP-encoding plasmid (10 ng/$\mu$l) as an indicator of successful injection. The relevant empty vector (pcDNA3.1 or pCR3.1) without the insert, as well as uninjected controls were always included. When neurotrophic factor-deprived neurons were analysed, the factor-maintained uninjected neurons were always included to show that the neurons do not die due to poor culture conditions. Neurons tolerating the injection procedure were counted 4-6 h later according to the map drawn with the help of squares scratched to the bottom of the culture dish, and considered as initial neurons. Next morning, the few living injected neurons that did not show GFP fluorescence, were subtracted from the initial neurons. An average, 25-80 neurons were successfully injected per experimental point. All experiments were repeated at least three times on the independent cultures. The results were expressed as mean±the standard error of the mean and were tested for the significance by either one-way ANOVA and post hoc Tukey's honestly significant difference test, or two tailed Student's t test with two sample unequal variance. The null hypothesis was rejected at $P<0.05$.

The following expression plasmids were injected: full-length human Bax and full-length human Bcl-$x_L$ expression plasmids, dominant negative FADD plasmid, Cys287Ala mutant of caspase 9, Cys320Ser mutant of mouse caspase-2, and plasmid for Ku70. Also, the expression plasmids for human XIAP (Yu et al., 2003) and dominant negative mutants of caspase-3, caspase-6, caspase-7 and caspase-8 (active center cysteine mutated to alanine in all cases) (Forcet et al., 2001) were used.

Immunocytochemistry

The neurons were grown on round glass coverslips, fixed with fresh 4% paraformaldechyde in phosphate-buffered saline, permeabilized with 1% Triton X-100 and blocked with 5% of donkey serum (Jackson ImmunoResearch Laboratories) in PBS. Antibodies to the following antigens were used: cytochrome c (65971A; BD PharMingen), phosphorylated serine 63 of c-Jun (9261; Cell Signaling Technology), phosphorylated serine 73 of c-Jun (9169; Cell Signaling Technology). Cy3-conjugated secondary antibodies (Jackson ImmunoResearch) were used for visualization and the specimens were mounted in Vectashield (Vector Laboratories). Images were captured at room temperature with DM-IRB inverted microscope (Leica) using PL FLUOTAR objective (63 x/0.70) or, for FIG. 2 A, HC PL FLUOTAR (10 x/0.30), a 3CCD color video camera (model DXC-950P) (Sony) under the control of Image-Pro Plus software version 3.0 (Media Cybernetics). Individual images were processed and assembled with Photoshop 7.0 (Adobe Systems). In some experiments, the fixed cultures were treated with 1 µg/ml of Hoechst 33258 (Molecular Probes) for 15 minutes, then mounted and observed for the nuclear morphology.

Electron Microscopy

The neurons were grown in the four-well plates (Nunc) and deprived of neurotrophic factors. The medium of the control neurons was also changed and the factors were added back. The cultures were fixed 48 h after neurotrophic factor deprivation with 2% of glutaraldehyde. To avoid detachment of loosely attached dying neurons, fixative with two-fold strength was carefully added to the culture medium. The cultures were then processed for transmission electron microscopy as described (Yu et al., 2003). From each sample, we chose one section cut from the middle third of the depth of the neuron, and all neurons within that section were analysed by FEI Tecnai F12 transmission electron microscope (Philips Electron Optics, Holland), operated at 80 kV. In two independent experiments, altogether 39 GDNF-deprived, 63 NGF-deprived, 25 GDNF-maintained and 39 NGF-maintained neurons were analysed. Very similar results were obtained from two independent experiments. For estimation of the size of mitochondria from GDNF- or NGF-deprived neurons, mitochondria at a final magnification of ×33,000 were manually traced onto transparencies that were scanned. Cross-sectional area of the mitochondria was measured using Image-Pro Plus version 3.0.

Western Blotting

The neurons were grown with GDNF or NGF for 6 days, then either deprived from these factors or not deprived for 14-18 h or 48 h in the presence of caspase inhibitor BAF. The cells were collected in the Laemmli sample buffer, lysed for 1 h on ice and analysed for Westen blotting using standard techniques. The filters were sequentially probed with antibodies to c-Jun (sc-45; Santa Cruz Biotechnology, Inc.), phosphorylated serine 63 of c-Jun (Cell Signaling Technology) and phosphorylated serine 73 of c-Jun (Cell Signaling Technology).

Results

One Third of Neonatal Rat Superior Cervical Ganglion Neurons are GDNF-Responsive When sympathetic neurons from one- or two-day-old rat superior cervical ganglion (SCG) were cultured with GDNF, the number of neurons gradually and slowly decreased. By sixth day in vitro (DIV), about 34% of the initially plated neurons had survived and this number did not decrease further (FIG. 1 A). In similar conditions, about 98% of the NGF-maintained neurons had survived (FIG. 1 A). Dose-dependence study revealed that 100 ng/ml was a saturating concentration of GDNF for SCG neurons (FIG. 1 B). Removal of GDNF from the six DIV cultures leads to death of the neurons that was kinetically similar to the death of NGF-deprived neurons (FIG. 1 C). In all studies described below, the neurons from newborn rat SCG were maintained in sister dishes with GDNF (100 ng/ml) or NGF (30 ng/ml) for six DIV, then deprived of these factors for 48 or 72 hours, and analysed. NGF- and GDNF-responsive neurons were always analysed in parallel and received identical treatment. The GDNF-responsive neurons appeared morphologically indistinguishable from NGF-responsive neurons. However, the data obtained from GDNF-responsive neurons were generally more variable, and more cultures failed, when compared to NGF-responsive neurons. Also, small number of neurons in the GDNF-deprived dishes seemed to die non-specifically due to the washing procedure. Thus, GDNF-responsive neurons seem to be more sensitive to small variations in the culture conditions, than NGF-responsive neurons.

Figures 2A, 2B:
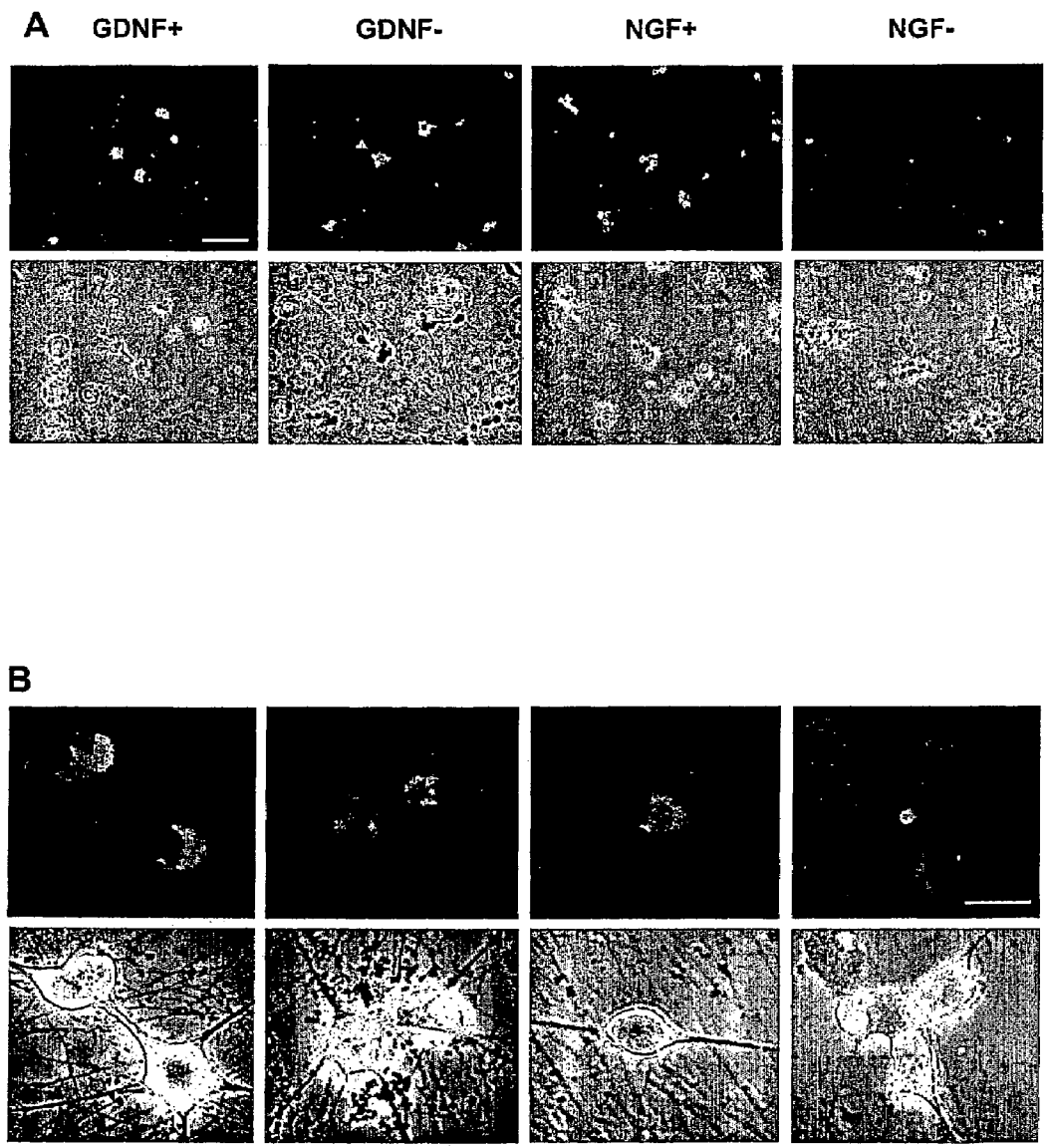
FIGS. 2A, 2B, and 2C. Cytochrome c is not released from the mitochondria of GDNF-deprived sympathetic neurons. (2A) Upper row, micrographs of the neurons deprived of GDNF or NGF for 48 h in the presence of caspase inhibitor BAF, or maintained with these factors, and immunostained with cytochrome c antibodies. Corresponding phase contrast images are shown on the lower row. Note that weak and diffuse immunostaining is barely visible on the NGF-deprived neurons, whereas almost all GDNF-deprived neurons stain strongly, as the neurons maintained with the factors. Scale bar: 100 μm. (2B) Upper row, typical cytochrome c immunostaining patterns of GDNF- or NGF-deprived or -maintained neurons. Corresponding phase contrast images are shown on the lower row. Note that in spite of pyknotic appearance, the GDNF-deprived neurons show strong punctate immunostaining (mitochondrial localization), whereas the NGF-deprived neurons stain weakly and diffusely (cytosolic localization). Levels of the images were equally enhanced with Adobe Photoshop software. Scale bar: 10 μm. (2C) Quantitation of the neurons deprived of neurotrophic factors for 48 h with or without BAF and having punctate pattern of cytochrome c immunostaining, calculated as percent of all neurons. Experiments with or without BAF were performed separately (four independent experiments for both) and combined to the same figure. The mean±standard error is shown for each data point. Statistical significance of the differences between factor-maintained and -deprived groups was estimated by Student's t test.
Figure 2C:
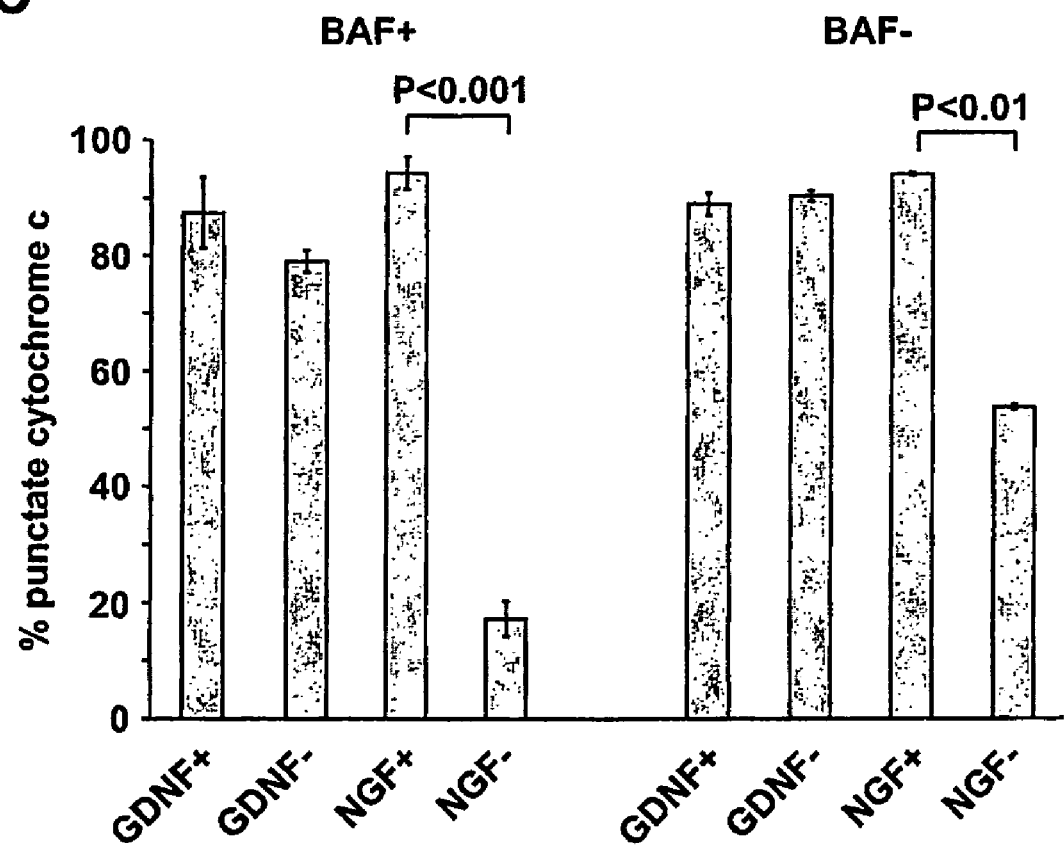

Mitochondrial Death Pathway is Not Activated in GDNF-Deprived Sympathetic Neurons To study the localization of cytochrome c, we removed GDNF or NGF from the respective neurons for 48 h in the presence of broad-range caspase inhibitor BAF, and stained the neurons with anti-cytochrome c antibodies. Only a small number of GDNF-deprived neurons showed faint diffuse cytochrome c staining characteristic of its cytosolic localization (FIG. 2). In contrast, removal of NGF dramatically reduced the number of neurons, with punctate mitochondrial cytochrome c localization (FIG. 2), as shown by others (Deshmukh and Johnson, 1998; Neame et al., 1998; Martinou et al., 1999). Similar results were obtained at 72 h after neurotrophic factor deprivation (not shown).

Figures 3A, 3B:
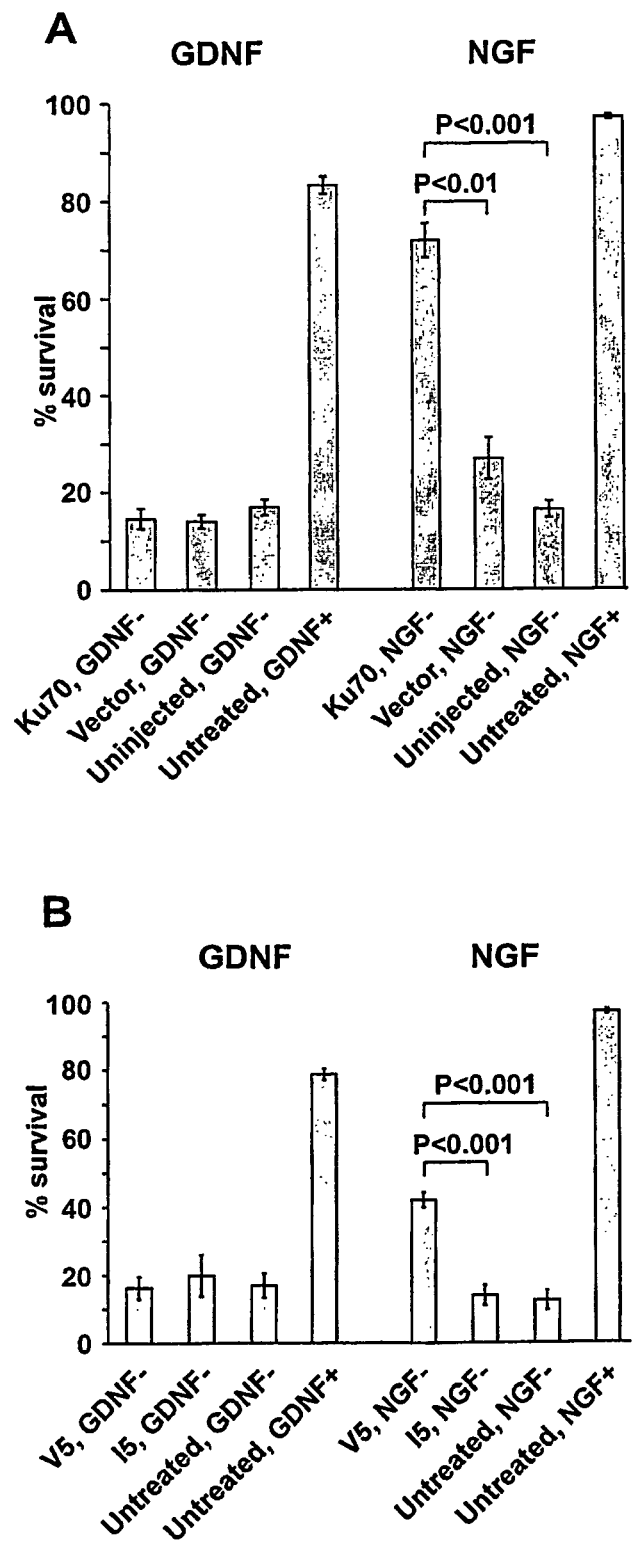
FIGS. 3A and 3B. Bax is not required for death of GDNF-deprived sympathetic neurons. (3A) GDNF- or NGF-deprived neurons were microinjected with expression plasmids for Ku70 or empty vector. (B) Neurons were deprived of GDNF or NGF in the presence of Ku70-derived Bax-blocking peptide V5 or control peptide I5. In (3A and 3B), living neurons were counted 72 h later and expressed as percent of initial neurons. The mean±standard error of the mean of three (3A) or four (3B) independent experiments is shown for each data point. Statistical significance of the differences was estimated by one-way ANOVA and post hoc Tukey's honestly significant difference test.

The role of Bax in the GDNF-deprived neurons was studied by overexpressing Ku70, a protein that was recently shown to bind the N-terminus of Bax, thereby inhibiting its translocation to the mitochondria (Sawada et al., 2003a; Sawada et al., 2003b). Ku70 had no effect on the death of GDNF-deprived neurons, although it significantly blocked the death of NGF-deprived neurons at 72 hours (FIG. 3 A). Similar effect was achieved with the Ku70-derived cell permeable peptide V5 shown to block the activity of Bax (Sawada et al., 2003a), whereas the control peptide I5 had no effect (FIG. 3 B).

Figure 4:
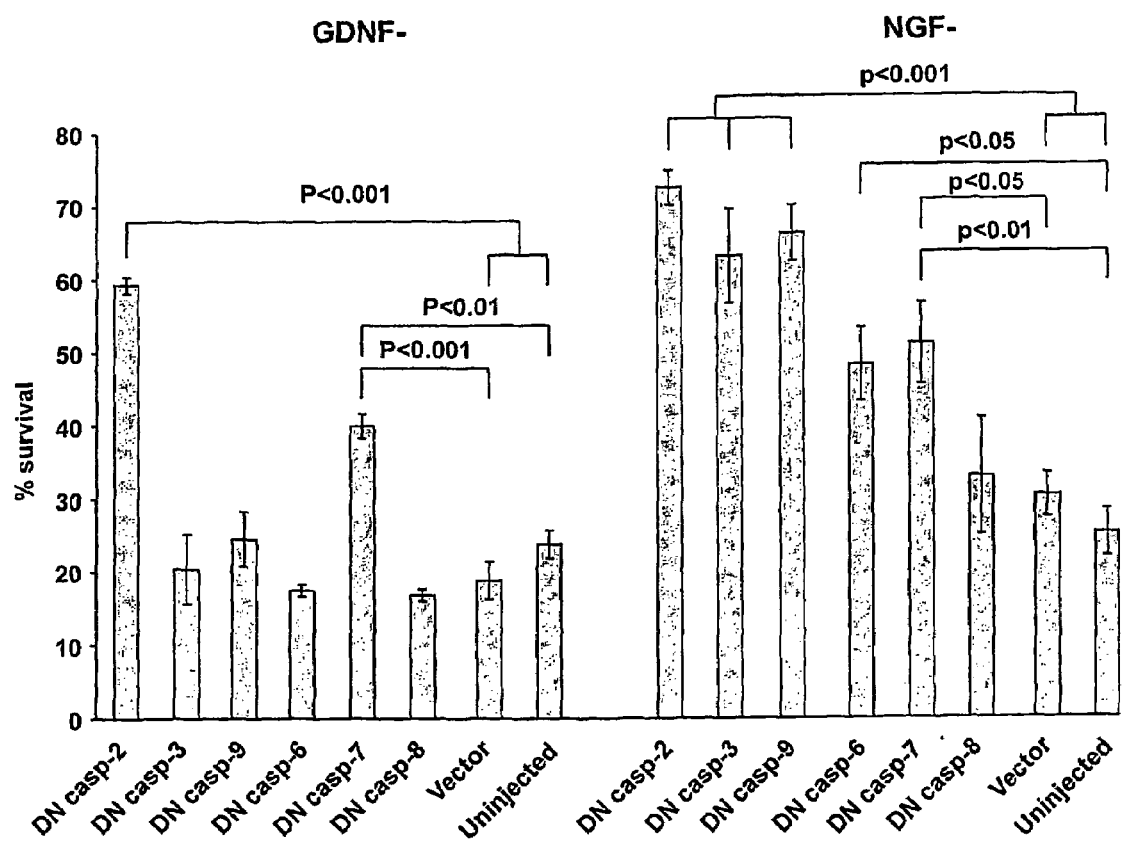
FIG. 4. Inhibition of individual caspases in GDNF- or NGF-deprived sympathetic neurons. GDNF- or NGF-selected sympathetic neurons were microinjected with expression plasmids for dominant negative (DN) mutants of indicated caspases and the neurotrophic factors were then deprived. Living neurons were counted 72 h later and expressed as percent of initial neurons. The mean±standard error of the mean of three (four for DN caspase-9) independent cultures is shown for each data point. Individual caspases were studied in different experiments and are combined to the same figure. Data of each DN-caspase were compared to averaged vector-controls and uninjected controls by one-way ANOVA and post hoc Tukey's honestly significant difference test.

Involvement of caspase-9 and caspase-3 in the death of neurotrophic factor-deprived sympathetic neurons was then investigated. However, direct demonstration of activation of the caspases by Western blotting appeared impossible due to scarcity of the material. Therefore we overexpressed dominant negative mutants of these caspases in GDNF- or NGF-deprived neurons. Inhibition of either caspase-9 or caspase-3 failed to inhibit the death of GDNF-deprived neurons, although they efficiently blocked death of NGF-deprived neurons by 72 h after microinjection and NGF deprivation (FIG. 4).

The absence of cytochrome c release together with a failure to observe the role of Bax, caspase-9 and caspase-3 suggest that GDNF-deprived neurons die via a nonmitochondrial pathway. To confirm this, we overexpressed the anti-apoptotic Bcl-2 family member Bcl-$x_L$, shown to block the mitochondrial death pathway, in the GDNF- and NGF-deprived neurons. Overexpressed Bcl-$x_L$ did not rescue GDNF-deprived neurons (FIG. 5 A), further confirming that the mitochondrial death pathway is not activated. Bcl-$x_L$, however, efficiently blocked the death of NGF-deprived neurons (FIG. 5 A), as also shown by others (Gonzalez-Garcia et al., 1995). GDNF-maintained neurons were killed by overexpressed pro-apoptotic protein Bax (FIG. 5 A), and Bax accelerated the death of GDNF-deprived neurons (not shown).

Caspase-2 and Caspase-7 are Activated in GDNF-Deprived Sympathetic Neurons

The broad-range caspase inhibitor BAF almost completely blocked death of both GDNF-deprived (FIG. 5 B) and NGF-deprived (FIG. 5 B) (Deshmukh et al., 1996; Martinou et al., 1999; Deshmukh et al., 2000) neurons showing that some caspases are absolutely required for the death of GDNF-deprived neurons. To identify the relevant caspases, we overexpressed by microinjection the dominant negative mutants of caspase-2, -3, -6, -7 and -8 in the GDNF-deprived, but also NGF-deprived neurons. Blocking of caspase-2 and, to lesser extent, caspase-6 and caspase-7 significantly inhibited death of NGF-deprived neurons, whereas dominant negative caspase-8 had no effect (FIG. 4). A dominant negative mutant of caspase-2, and to lesser extent, caspase-7, also inhibited death of GDNF-deprived neurons, whereas blocking of caspase-6 and caspase-8 had no effect (FIG. 4). Thus, GDNF deprivation-induced death requires caspase-2 and caspase-7 in sympathetic neurons.

Caspase-2 was recently shown to be activated upstream of the mitochondria, and this event was required for the permeabilization of the mitochondria (Lassus et al., 2002). The presence of BAF in our culture medium may thus, via inhibition of caspase-2, block cytochrome c release in GDNF-deprived neurons and force them to chose another pathway. We therefore deprived the neurons of neurotrophic factors without BAF and applied cytochrome c immunocytochemistry. Although many neurons have disappeared, cytochrome c immunostaining was still mostly punctuate in the remaining GDNF-deprived neurons (and in about half of the remained NGF-deprived neurons) (FIG. 2 C).

We also overexpressed the X chromosome-linked Inhibitor of Apoptosis Protein (XIAP), a natural inhibitor of caspases, in GDNF- and NGF-deprived neurons. XIAP did not affect the death of GDNF-deprived neurons (FIG. 5 C) although, as expected (Yu et al., 2003), it rescued significant portion of NGF-deprived neurons (FIG. 5 C). Overexpression of XIAP did not significantly affect the viability of NGF-maintained or GDNF-maintained neurons (not shown). Thus, the caspases that execute death of GDNF-deprived neurons could not be blocked by overexpressed XIAP.

c-Jun is Required for the Death of, and is Differently Activated in GDNF-Deprived and NGF-Deprived Sympathetic Neurons To study the activation of the transcription factor c-Jun, we deprived GDNF- or NGF-responsive BAF-saved neurons from the respective factors for 48 h, stained the neurons with antibodies to phosphorylated serines 63 or 73, and counted the neurons with strong nuclear immunoreactivity. Deprivation of GDNF significantly increased the number of neurons immunopositive for phosphorylated serine 73 (FIG. 6 A). However, the number of nuclei positive for phosphorylated serine 63 was unchanged in the GDNF-deprived neurons (FIG. 6 A, B). In control cultures, deprivation of NGF dramatically induced phosphorylation of serine 63 of c-Jun, as shown by others (Ham et al., 1995; Virdee et al., 1997; Eilers et al., 1998; Harris et al., 2002), but also of serine 73 (FIG. 6 A, B) (Besirli and Johnson, 2003). As expected, only faint staining was obtained for the neurons maintained in the presence of GDNF or NGF (FIG. 6 A). Similar results were obtained at 72 h after neurotrophic factor deprivation (not shown).

In summary, our data show that activation of c-Jun is necessary for the death of GDNF-deprived neurons, although it is activated differently from NGF-deprived neurons.

Death Receptor Pathway is not Activated in GDNF-Deprived Sympathetic Neurons

The data presented above show that GDNF-deprived sympathetic neurons die via a nonmitochondrial death pathway where c-Jun, as well as caspase-2 and caspase-7 are involved. Another well-characterized pathway, the death receptor-mediated pathway can be efficiently blocked by dominant negative mutant of FADD/MORT1, an adapter that links procaspase-8 to most death receptors (Vincenz, 2001; Strasser and Newton, 1999). Overexpression of this mutant FADD in GDNF-deprived, but also in NGF-deprived sympathetic neurons did not change the death rate (FIG. 5 D), neither did it affect the viability of neurons maintained with NGF or GDNF (not shown). Also, as shown above, overexpression of dominant negative caspase-8 did not affect death of neurons deprived of either factor (FIG. 4). Thus, the death receptor pathway is probably not activated in the NGF- or GDNF-deprived sympathetic neurons. In accordance with that, activation of death receptors tumor necrosis factor-α or Fas on the surface of NGF-maintained sympathetic neurons did not induce their death Putcha et al., 2002).

Ultrastructure of GDNF-Deprived and NGF-Deprived Sympathetic Neurons

To investigate the ultrastructural changes caused by removal of GDNF or NGF in sympathetic neurons, we deprived the cultures of neurotrophic factors for 48 h and analysed the neurons by transmission electron microscopy. Neurons maintained with GDNF or NGF were analysed as well. As a general observation, the cytoplasm of GDNF-deprived neurons was much more electron-dense than that of NGF-deprived neurons in the sister culture or the neurons maintained with either neurotrophic factor. Removal of GDNF led to marked increase in the number of different autophagic profiles, including double-membraned autophagosomes and single-membraned autolysosomes that often contained swirled packs of undigested membranes (FIG. 7). Thus, on average, 9 autolysosomes per neuron but no autophagosomes were found in GDNF-maintained neurons (n=25), whereas, on average, 3 autophagosomes and 14 autolysosomes were found per GDNF-deprived neuron (n=39). NGF-deprived neurons also exhibited an increased number of autolysosomes (average of 18 per NGF-deprived neuron; n=63 versus 9 per NGF-maintained neuron; n=39) but the autophagosomes were only rarely found (0.3 per average NGF-deprived neuron and none in NGF-maintained neurons). Normal endoplasmic reticulum and Golgi complex were still found in the GDNF- and NGF-deprived neurons with enhanced autophagy.

The mitochondria of GDNF-deprived neurons (FIG. 8 A) were similar to those of GDNF-maintained (and also NGF-maintained) neurons (not shown), having mostly the orthodox configuration including elongated shape and clear cristae, and were not clustered. Such normal mitochondria were found in all GDNF-deprived neurons, including those with massive autophagy (FIG. 8 A). However, the mitochondria in NGF-deprived neurons were often round-shaped and clustered (FIG. 8 B). The cristae of such mitochondria were markedly reorganized, often observed to be round, vesicular and rare in the number, and sometimes only one mitochondrial membrane was discernible (FIG. 8 C). Some mitochondria in these clusters contained different numbers of normal rod-like cristae along with the mitochondria with changed vesicular cristae (FIG. 8 D). In many neurons with such mitochondrial clusters, few elongated nonclustered mitochondria with the orthodox configuration were found, whereas some neurons contained only normal mitochondria (not shown). Of all NGF-deprived neurons analysed in two experiments (n=63), 43% had round-shaped, clustered mitochondria with changed cristae, 19% had the mitochondria in orthodox configuration, and in 38%, both types of mitochondria were found. Appearance of the round clustered mitochondria seems not to be a feature of final death phase, as these were often found in neurons with normal endoplasmic reticulum, Golgi complex, and nucleus without condensed chromatin. We did not observe swelling and disruption of the mitochondria in NGF-deprived neurons.

The average cross-sectional area of the mitochondria was 0.0781±0.0039 µm² (mean±S.E.M., n=201) in the GDNF-deprived neurons and 0.038±0.0013 µm² (n=317) in the NGF-deprived neurons. These values, as determined from thin sections, do not directly indicate the length or size of the mitochondria. In each section there is a collection of profiles from smallest perpendicular round profiles to longer oval-shape or even branched profiles depending of the orientation of the mitochondria in relation to sectioning angle. To illustrate the difference in the size of the mitochondria we plotted the distribution of profiles according to their cross-sectional area (FIG. 8 E). About 50% of all profiles in sections from the NGF-deprived neurons fit into category of 0.02-0.04 µm² and there were few profiles larger than 0.12 µm², whereas broad range of mitochondrial profiles up to 0.3 µm² and larger were found from the GDNF-deprived neurons.

We did not found nuclei with condensed chromatin in the GDNF-deprived neurons, analysed by electron microscopy, although 24% of the NGF-deprived neurons had the nuclei with DNA condensed to different extent (not shown). We also stained the neurons maintained with or deprived of GDNF or NGF with Hoechst 33258 and counted the neurons having typical fragmented nuclei with condensed chromatin. As shown on FIG. 9, progressively increasing number of NGF-deprived neurons with apoptotic nuclei was observed during three-day period, whereas only small fraction (5-7%) of the GDNF-deprived or -maintained neurons had fragmented nuclei. This number did not increase with time and most probably shows nonspecific death. Virtually all NGF-maintained neurons had normal nuclei (not shown). Thus, we did not observe nuclear changes in the GDNF-deprived neurons.

Discussion

We found that removal of GDNF from the cultured sympathetic neurons triggers a novel nonmitochondrial MLK-, c-Jun- and caspase-dependent death pathway, although removal of NGF from the sympathetic neurons activates the mitochondrial pathway. This is to our knowledge, the first description of a nonmitochondrial pathway activated by withdrawal of a survival factor.

GDNF Deprivation-Induced Death Requires MLK-c-Jun Pathway, Caspases-2 and -7, and Involves Increased Autophagy The mitochondrial pathway is not activated in GDNF-deprived sympathetic neurons. Indeed, cytochrome c is not released from the mitochondria to cytosol, Bax, caspases-9 and -3 are not involved in death execution, overexpression of Bcl-$x_L$ does not protect the neurons, and the ultrastructure of the mitochondria in GDNF-deprived neurons is not changed. We have currently found several proteins involved in the death of GDNF-deprived neurons. MLK and c-Jun are activated and seem to be similarly required for death of both NGF- and GDNF-deprived neurons. Surprisingly we did not detect increase in phospho-serine 63 immunoreactivity of c-Jun in GDNF-deprived neurons, although both serines 63 and 73 were phosphorylated in NGF-deprived neurons. The kinases that phosphorylate c-Jun in GDNF-deprived neurons remain to be studied.

Caspase-2 and caspase-7 are involved in the death of GDNF-deprived sympathetic neurons. Very little is known about the mechanism of caspase-2 activation. However, it is tempting to speculate that caspase-2 functions as an initiator and caspase-7 an executioner in these neurons. Recent reports that caspase-2 is activated upstream of mitochondrial events in some apoptotic cell types (Guo et al., 2002; Lassus et al., 2002; Read et al., 2002) are in accordance with our data. Overexpressed XIAP did not rescue GDNF-deprived neurons, although XIAP can inactivate caspase-7 in cell-free systems (Deveraux et al., 1997) suggesting that caspase-7 is not available for XIAP in the GDNF-responsive sympathetic neurons. It should also be stressed that, although the dominant-negative caspase isoforms used here should be specific for given caspases, some non-specific effects cannot be completely excluded.

Many cells in which the main mitochondrial death pathway is genetically or pharmacologically disabled can still die via an alternative, autophagic pathway that is often caspase-independent and with increased autophagy leading to largely vacuolised cytoplasm (Sperandio et al., 2000; Yaginuma et al., 2001; Oppenheim et al., 2001; Zaidi et al., 2001; Marsden et al., 2002). Dying GDNF-deprived neurons, however, seem to differ from those "classical" autophagic death patterns, as the caspases are clearly involved. We indeed observed markedly increased autophagy in the GDNF-deprived neurons, but no remarkable vacuolisation of the cytoplasm was found, at least before the short final death execution phase. Few neurons in the terminal state of death that were retained in our electron microscopic preparations showed typical features of secondary necrosis, similar for both GDNF- and NGF-deprived neurons (data not shown). We found increased autophagy also in the NGF-deprived neurons, as described by others (Martinou et al., 1999; Xue et al., 1999; Kirkland et al., 2002). Thus, both NGF- and GDNF-deprived neurons die in a caspase-dependent manner with enhanced autophagy.

NGF-Deprived Sympathetic Neurons Die via Mitochondrial Pathway

We confirmed the published data that NGF-deprived neurons die via the mitochondrial pathway, including cytosolic localization of cytochrome c (Deshmukh and Johnson, 1998; Neame et al., 1998; Martinou et al., 1999), involvement of Bax (Deckwerth et al., 1996; Putcha et al., 1999), caspase-9 and caspase-3 (Deshmukh et al., 2000; Deshmukh et al., 2002) and inhibition of death by Bcl-$x_L$ (Gonzalez-Garcia et al., 1995). In addition, we showed for the first time that also caspase-6 and caspase-7 are necessary for NGF deprivation-induced death, and confirmed the role of caspase-2 (Troy et al., 2001).

Our overexpression studies (Yu et al., 2003); this study) are in agreement with the current concept that in NGF-responsive sympathetic neurons, critical caspases are blocked with Inhibitor of Apoptosis Proteins, e.g. XIAP. Withdrawal of NGF releases caspases from that block by proteasome-mediated degradation, but also by removal of XIAP from the caspases by Smac/DIABLO that is released from the mitochondria together with cytochrome c (Troy et al., 2001; Deshmukh et al., 2002; Yu et al., 2003). Most probably a large amount of overexpressed XIAP replaces the degraded bulk and keeps the caspases inactivated in our experiment.

We found remarkable ultrastructural changes in the mitochondria of many NGF-deprived neurons: they gradually become round, clustered and their cristae changed considerably. Appearance of round mitochondria as a result of increased fission has been described previously in the NGF-deprived neurons (Martinou et al., 1999) and in other cells (Karbowski et al., 2002). Also, the clustering of mitochondria in NGF-deprived neurons has been described (Tolkovsky et al., 2002), although the mechanism remained obscure. However, our observation that the cristae in the small clustered mitochondria of NGF-deprived neurons were often round, vesicular, and reduced whereas the inner membrane was sometimes found to be missing, have not been described in other studies (Martin et al., 1988; Martinou et al., 1999; Xue et al., 1999; Kirkland et al., 2002). We do not know whether this discrepancy results from differences in the culture conditions, genetic background of the animals, or from other conditions, but this ultrastructural pattern was repeatedly observed in our cultures. Mitochondria with orthodox and altered ultrastructure were found in the same sample, sometimes even in the same neuron, ruling out the possibility of a processing artifact. The mitochondrial cristae are dynamic structures that can considerably change their shape (Frey et al., 2002). In the apoptotic cells, these changes are proposed to facilitate the release of cristae-associated cytochrome c into the intermembrane space (Scorrano et al., 2002). It is tempting to speculate that the mitochondria with altered cristae have already released their cytochrome c. We also stress that our data do not support the release of apoptotic proteins from the mitochondria via their swelling and rupture.

In summary, we propose that GDNF-deprived sympathetic neurons die by caspase-dependent nonmitochondrial death pathway that has not been described previously. More studies are required to characterize the molecular and cellular components of this pathway. How an exposure of SCG neurons to different neurotrophic factors dictates the death program, is currently unknown. It was recently shown that an apoptotic fragment, generated from unligated Ret by caspase-3, can trigger apoptosis in some cell lines (Bordeaux et al., 2000). However, overexpression of Ret or apoptotic fragment of Ret in the sympathetic neurons did not induce their death in our model (unpublished data), suggesting that death-promoting activity of unligated Ret is not manifested in the sympathetic neurons. Ret, similarly to Deleted in Colorectal Cancer (Forcet et al., 2001), may be able to recruit and activate caspases directly, so that mitochondrial pathway is not required. Alternatively, exposure of the neurons to GDNF for six days may differentiate the neurons so that the mitochondrial pathway is nonfunctional. Whether and how the nonmitochondrial death pathway is used in vivo is currently unknown, as virtually nothing is yet known about the biological role of GDNF for the SCG neurons.

Some of the abbreviations used herein: NGF, nerve growth factor; GDNF, glial cell line-derived neurotrophif factor; SCG, superior cervical ganglion; DIV, days in vitro; BAF, boc-aspartyl(OMe)-fluoromethylketone; XIAP, X chromosome-linked inhibitor of apoptosis protein; BDNF, brain-derived neurotrophic factor.

REFERENCES

1. Airaksinen, M. S. and M. Saarma. 2002. The GDNF family: signalling, biological functions and therapeutic value. *Nat. Rev. Neurosci.* 3:383-394.
2. Besirli, C. G. and E. M. Johnson, Jr. 2003. JNK-independent activation of c-Jun during neuronal apoptosis Induced by multiple DNA-damaging agents. *J. Biol. Chem.* 278:22357-22366.
3. Bordeaux, M. C., C. Forcet, L. Granger, V. Corset, C. Bidaud, M. Billaud, D. E. Bredesen, P. Edery, and P. Mehlen. 2000. The RET proto-oncogene induces apoptosis: a novel mechanism for Hirschsprung disease. *EMBO J.* 19:4056-4063.
4. Clarke, P. G. 1990. Developmental cell death: morphological diversity and multiple mechanisms. *Anat. Embryol. (Berl)* 181:195-213.
5. Deckwerth, T. L., J. L. Elliott, C. M. Knudson, E. M. Johnson, Jr., W. D. Snider, and S. S. Korsmeyer. 1996. BAX is required for neuronal death after trophic factor deprivation and during development. *Neuron* 17:401-411.
6. Deshmukh, M. and E. M. Johnson, Jr. 1998. Evidence of a novel event during neuronal death: development of competence-to-die in response to cytoplasmic cytochrome c. *Neuron* 21:695-705.
7. Deshmukh, M., J. Vasilakos, T. L. Deckwerth, P. A. Lampe, B. D. Shivers, and E. M. Johnson, Jr. 1996. Genetic and metabolic status of NGF-deprived sympathetic neurons saved by an inhibitor of ICE family proteases. *J. Cell Biol.* 135:1341-1354.
8. Deshmukh, M., C. Du, X. Wang, and E. M. Johnson, Jr. 2002. Exogenous Smac induces competence and permits caspase activation in sympathetic neurons. *J. Neurosci.* 22:8018-8027.
9. Deshmukh, M., K. Kuida, and E. M. Johnson. 2000. Caspase inhibition extends the commitment to neuronal death beyond cytochrome c release to the point of mitochondrial depolarization. *J. Cell Biol.* 150:131-144.
10. Deveraux, Q. L., R. Takahashi, G. S. Salvesen, and J. C. Reed. 1997. X-linked IAP is a direct inhibitor of cell-death proteases. *Nature* 388:300-304.
11. Edwards, S. N. and A. M. Tolkovsky. 1994. Characterization of apoptosis in cultured rat sympathetic neurons after nerve growth factor withdrawal. *J. Cell Biol.* 124:537-546.
12. Eilers, A., J. Whitfield, C. Babij, L. L. Rubin, and J. Ham. 1998. Role of the Jun kinase pathway in the regulation of c-Jun expression and apoptosis in sympathetic neurons. *J. Neurosci.* 18:1713-1724.
13. Ellerby, L. M., A. S. Hackam, S. S. Propp, H. M. Ellerby, S. Rabizadeh, N. R. Cashman, M. A. Trifiro, L. Pinsky, C. L. Wellington, G. S. Salvesen, M. R. Hayden, and D. E. Bredesen. 1999. Kennedy's disease: caspase cleavage of the androgen receptor is a crucial event in cytotoxicity. *J. Neurochem.* 72:185-195.
14. Estus, S., W. J. Zaks, R. S. Freeman, M. Gruda, R. Bravo, and E. M. Johnson, Jr. 1994. Altered gene expression in neurons during programmed cell death: identification of c-jun as necessary for neuronal apoptosis. *J. Cell Biol.* 127:1717-1727.
15. Forcet, C., X. Ye, L. Granger, V. Corset, H. Shin, D. E. Bredesen, and P. Mehlen. 2001. The dependence receptor DCC (deleted in colorectal cancer) defines an alternative mechanism for caspase activation. *PNAS* 98:3416-3421.
16. Frey, T. G., C. W. Renken, and G. A. Perkins. 2002. Insight into mitochondrial structure and function from electron tomography. *Biochimica et Biophysica Acta (BBA)—Bioenergetics* 1555:196-203.
17. Gonzalez-Garcia, M., I. Garcia, L. Ding, S. O'Shea, L. H. Boise, C. B. Thompson, and G. Nunez. 1995. bcl-x is expressed in embryonic and postnatal neural tissues and functions to prevent neuronal cell death. *PNAS* 92:4304-4308.
18. Guo, Y., S. M. Srinivasula, A. Druilhe, T. Fernandes-Alnemri, and E. S. Alnemri. 2002. Caspase-2 induces apoptosis by releasing proapoptotic proteins from mitochondria. *J. Biol. Chem.* 277:13430-13437.
19. Ham, J., C. Babij, J. Whiffield, C. M. Pfarr, D. Lallemand, M. Yaniv, and L. L. Rubin. 1995. A c-Jun dominant negative mutant protects sympathetic neurons against programmed cell death. *Neuron* 14:927-939.

20. Hamner, S., U. Arumäe, Y. Li-Ying, Y. F. Sun, M. Saarma, and D. Lindholm. 2001. Functional characterization of two splice variants of rat bad and their interaction with Bcl-w in sympathetic neurons. *Mol. Cell Neurosci.* 17:97-106.
21. Harris, C. A., M. Deshmukh, B. Tsui-Pierchala, A. C. Maroney, and E. M. Johnson, Jr. 2002. Inhibition of the c-Jun N-terminal kinase signaling pathway by the mixed lineage kinase inhibitor CEP-1347 (KT7515) preserves metabolism and growth of trophic factor-deprived neurons. *J. Neurosci.* 22:103-113.
22. Huang, E. J. and L. F. Reichardt. 2001. Neurotrophins: roles in neuronal development and function. *Annu. Rev. Neurosci.* 24:677-736.
23. Karbowski, M., Y. J. Lee, B. Gaume, S. Y. Jeong, S. Frank, A. Nechushtan, A. Santel, M. Fuller, C. L. Smith, and R. J. Youle. 2002. Spatial and temporal association of Bax with mitochondrial fission sites, Drp1, and Mfn2 during apoptosis. *J. Cell Biol.* 159:931-938.
24. Kirkland, R. A., R. M. Adibhatla, J. F. Hatcher, and J. L. Franklin. 2002. Loss of cardiolipin and mitochondria during programmed neuronal death: evidence of a role for lipid peroxidation and autophagy. *Neuroscience* 115: 587-602.
25. Kotzbauer, P. T., P. A. Lampe, R. O. Heuckeroth, J. P. Golden, D. J. Creedon, E. M. Johnson, Jr., and J. Milbrandt. 1996. Neurturin, a relative of glial-cell-line-derived neurotrophic factor. *Nature* 384:467-470.
26. Lassus, P., X. Opitz-Araya, and Y. Lazebnik. 2002. Requirement for caspase-2 in stress-induced apoptosis before mitochondrial permeabilization. *Science* 297: 1352-1354.
27. Leist, M. and M. Jäättelä. 2001. Four deaths and a funeral: from caspases to alternative mechanisms. *Nat. Rev. Mol. Cell Biol.* 2:589-598.
28. Lindahl, M., D. Poteryaev, L. Yu, U. Arumäe, T. Timmusk, I. Bongarzone, A. Aiello, M. A. Pierotti, M. S. Airaksinen, and M. Saarma. 2001. Human glial cell line-derived neurotrophic factor receptor alpha 4 is the receptor for persephin and is predominantly expressed in normal and malignant thyroid medullary cells. *J. Biol. Chem.* 276:9344-93511.
29. Llambi F., F. Causeret, E. Bloch-Gallego, and P. Mehlen. 2001. Netrin-1 acts as a survival factor via its receptors UNC5H and DCC. *EMBO J.* 20:2715.
30. Maroney, A. C., J. P. Finn, D. Bozyczko-Coyne, T. M. O'Kane, N. T. Neff, A. M. Tolkovsky, D. S. Park, C. Y. Yan, C. M. Troy, and L. A. Greene. 1999. CEP-1347 (KT7515), an inhibitor of JNK activation, rescues sympathetic neurons and neuronally differentiated PC12 cells from death evoked by three distinct insults. *J. Neurochem.* 73:1901-1912.
31. Maroney, A. C., J. P. Finn, T. J. Connors, J. T. Durkin, T. Angeles, G. Gessner, Z. Xu, S. L. Meyer, M. J. Savage, L. A. Greene, R. W. Scott, and J. L. Vaught. 2001. CEP-1347 (KT7515), a semisynthetic inhibitor of the mixed lineage kinase family. *J. Biol. Chem.* 276:25302-25308.
32. Marsden, V. S., L. O'Connor, L. A. O'Reilly, J. Silke, D. Metcalf, P. G. Ekert, D. C. Huang, F. Cecconi, K. Kuida, K. J. Tomaselli, S. Roy, D. W. Nicholson, D. L. Vaux, P. Bouillet, J. M. Adams, and A. Strasser. 2002. Apoptosis initiated by Bcl-2-regulated caspase activation independently of the cytochrome c/Apaf-1/caspase-9 apoptosome. *Nature* 419:634-637.
33. Martin, D. P., R. E. Schmidt, P. S. DiStefano, O. H. Lowry, J. G. Carter, and E. M. Johnson, Jr. 1988. Inhibitors of protein synthesis and RNA synthesis prevent neuronal death caused by nerve growth factor deprivation. *J. Cell Biol.* 106:829-844.
34. Martinou, I., S. Desagher, R. Eskes, B. Antonsson, E. Andre, S. Fakan, and J. C. Martinou. 1999. The release of cytochrome c from mitochondria during apoptosis of NGF-deprived sympathetic neurons is a reversible event. *J. Cell Biol.* 144:883-889.
35. Neame, S. J., L. L. Rubin, and K. L. Philpott. 1998. Blocking cytochrome c activity within intact neurons inhibits apoptosis. *J. Cell Biol.* 142:1583-1593.
36. Oppenheim, R. W., R. A. Flavell, S. Vinsant, D. Prevette, C. Y. Kuan, and P. Rakic. 2001. Programmed cell death of developing mammalian neurons after genetic deletion of caspases. *J. Neurosci.* 211:4752-4760.
37. Pittman, R. N., S. Wang, A. J. DiBenedetto, and J. C. Mills. 1993. A system for characterizing cellular and molecular events in programmed neuronal cell death. *J. Neurosci.* 13:3669-3680.
38. Putcha, G. V., M. Deshmukh, and E. M. Johnson, Jr. 1999. BAX translocation is a critical event in neuronal apoptosis regulation by neuroprotectants, BCL-2, and caspases. *J. Neurosci.* 19:7476-7485.
39. Putcha, G. V., C. A. Harris, K. L. Moulder, R. M. Easton, C. B. Thompson, and E. M. Johnson, Jr. 2002. Intrinsic and extrinsic pathway signaling during neuronal apoptosis: lessons from the analysis of mutant mice. *J. Cell Biol* 157:441-453.
40. Rabizadeh, S., J. Oh, L. T. Zhong, J. Yang, C. M. Bitler, L. L. Butcher, and D. E. Bredesen. 1993. Induction of apoptosis by the low-affinity NGF receptor. *Science* 261:345-348.
41. Read, S. H., B. C. Baliga, P. G. Ekert, D. L. Vaux, and S. Kumar. 2002. A novel Apaf-1-independent putative caspase-2 activation complex. *J. Cell Biol.* 159:739-745.
42. Sawada, M., P. Hayes, and S. Matsuyama. 2003a. Cytoprotective membrane-permeable peptides designed from the BAX-binding domain of Ku70. *Nat. Cell Biol.* 5:352-357.
43. Sawada, M., W. Sun, P. Hayes, K. Leskov, D. A. Boothman, and S. Matsuyama. 2003b. Ku70 suppresses the apoptotic translocation of Bax to mitochondria. *Nat. Cell Biol.* 5:320-329.
44. Scorrano, L., M. Ashiya, K. Buttle, S. Weiler, S. A. Oakes, C. A. Mannella, and S. J. Korsmeyer. 2002. A distinct pathway remodels mitochondrial cristae and mobilizes cytochrome c during apoptosis. *Dev. Cell* 2:55-67.
45. Sperandio, S., I. de Belle, and D. E. Bredesen. 2000. An alternative, nonapoptotic form of programmed cell death. *PNAS* 97:14376-14381.
46. Strasser, A. and K. Newton. 1999. FADD/MORT1, a signal transducer that can promote cell death or cell growth. *Int. J. Biochem. Cell Biol.* 31:533-537.
47. Sun, Y. F., L. Y. Yu, M. Saarma, T. Timmusk, and U. Arumäe. 2001. Neuron-specific Bcl-2 homology 3 domain-only splice variant of Bak is anti-apoptotic in neurons, but pro-apoptotic in non-neuronal cells. *J. Biol. Chem.* 276:16240-16247.
48. Thibert, C., M. A. Teillet, F. Lapointe, L. Mazelin, N. M. Le Douarin, and P. Mehlen. 2003. Inhibition of neuroepithelial patched-induced apoptosis by sonic hedgehog. *Science* 301:843-846.
49. Tolkovsky, A. M., L. Xue, G. C. Fletcher, and V. Borutaite. 2002. Mitochondrial disappearance from cells: a clue to the role of autophagy in programmed cell death and disease? *Biochimie* 84:233-240.

50. Troy, C. M., S. A. Rabacchi, J. B. Hohl, J. M. Angelastro, L. A. Greene, and M. L. Shelanski. 2001. Death in the balance: alternative participation of the caspase-2 and -9 pathways in neuronal death induced by nerve growth factor deprivation. *J. Neurosci.* 21:5007-5016.

51. Vincenz, C. 2001. Death receptors and apoptosis. Deadly signaling and evasive tactics. *Cardiol. Clin.* 19:31-43.

52. Virdee, K., A. J. Bannister, S. P. Hunt, and A. M. Tolkovsky. 1997. Comparison between the timing of JNK activation, c-Jun phosphorylation, and onset of death commitment in sympathetic neurones. *J. Neurochem.* 69:550-561.

53. Xue, L., G. C. Fletcher, and A. M. Tolkovsky. 1999. Autophagy is activated by apoptotic signalling in sympathetic neurons: an alternative mechanism of death execution. *Mol. Cell Neurosci.* 14:180-198.

54. Yaginuma, H., N. Shiraiwa, T. Shimada, K. Nishiyama, J. Hong, S. Wang, T. Momoi, Y. Uchiyama, and R. W. Oppenheim. 2001. Caspase activity is involved in, but is dispensable for, early motoneuron death in the chick embryo cervical spinal cord. *Mol. Cell Neurosci.* 18:168-182.

55. Yu, L., L. Korhonen, R. Martinez, E. Jokitalo, Y. Chen, U. Arumäe, and D. Lindholm. 2003. Regulation of sympathetic neuron and neuroblastoma cell death by XIAP and its association with proteasomes in neural cells. *Molecular and Cellular Neuroscience* 22:308-318.

56. Zaidi, A. U., C. D'Sa-Eipper, J. Brenner, K. Kuida, T. S. Zheng, R. A. Flavell, P. Rakic, and K. A. Roth. 2001. Bcl-$x_L$-caspase-9 interactions in the developing nervous system: evidence for multiple death pathways. *J. Neurosci.* 21:169-175.

57. Zimmermann, K. C., C. Bonzon, and D. R. Green. 2001. The machinery of programmed cell death. *Pharmacol. Ther.* 92:57-70.

The invention claimed is:

1. A method of screening caspase-2 and caspase-7-dependent cell death pathway modulators of neuronal cells in a glail cell line-derived neurotrophic factor (GDNF)-dependent cell culture system, comprising the steps of:
   removing GDNF from the culture system;
   introducing a candidate modulator agent into the culture system;
   determining the activity of at least caspase-2, caspase-3 and caspase-7 in a cultured neuronal cell from said culture system; and
   identifying said candidate modulator agent as a stimulator of caspase-2 and caspase-7-dependent cell death pathway, if the activity of caspase-2 and caspase-7, and/or the amount of caspase-2 and caspase-7 mRNA or protein is detected to be higher in the presence of the candidate modulator agent than in its absence and caspase-3 is determined to be not activated by the presence of the candidate modulator agent, or identifying said candidate modulator agent as an inhibitor of caspase-2 and caspase-7-dependent cell death pathway, if the activity of caspase-2 and caspase-7 and/or the amount of caspase-2 and caspase-7 mRNA or protein is detected to be lower in the presence of the candidate modulator agent than in its absence and caspase-3 is determined to be not activated by the presence of the candidate modulator agent.

2. The method according to claim 1, wherein said neuronal cells are selected from the group consisting of cervical ganglion neurons, dorsal root ganglion cells, nodose ganglion neurons, spinal motoneurons, midbrain dopaminergic neurons, central noradrenergic neurons and enteric neurons.

3. The method according to claim 1, wherein said candidate modulator agent is from a combinatorial library selected from the group consisting of: biological library; peptoid library, spatially addressable parallel solid phase library, solution phase library; synthetic library requiring deconvolution; "one-bead, one-compound" library; and synthetic library using affinity chromatography selection.

4. The method according to claim 3, wherein said combinatorial library is peptide library, non-peptide oligomer library or small molecule library.

5. The method according to claim 1, wherein the determining of the ability of the candidate modulator agent to modulate caspase-2 and caspase-7 activity comprises monitoring cell death, cell growth, cell attachment, neurite outgrowth, and/or cell chemotaxis.

6. The method according to claim 1, wherein the determining of the ability of the candidate modulator agent to modulate caspase-2 and caspase-7 activity comprises Western blot; immunohistochemical staining using anti caspase-2, caspase-3 or caspase-7 antibodies; and/or fluorometric assays.

7. The method according to claim 6, wherein said fluorometric assay is a fluorescence electron transfer (FRET)-assay.

8. The method according to claim 1, wherein the determining of the ability of the candidate modulator agent to modulate caspase-2 and caspase-7 activity comprises detecting catalytic or enzymatic activity of caspase-2, caspase-3 and caspase-7.

9. The method according to claim 1, wherein the determining of the ability of the candidate modulator agent to modulate caspase-2 and caspase-7 activity comprises detecting a target-regulated cellular response selected from the group consisting of cell attachment, cell adhesion, cell growth, cell death and cell migration.

10. The method according to claim 1, wherein the determining of the ability of the candidate modulator agent to modulate caspase-2 and caspase-7 activity comprises detecting the amount of caspase-2, caspase-3 and caspase-7 mRNA or protein in a cultured neuronal cell in the presence of the candidate modulator agent and comparing the detected amount to the amount of caspase-2, caspase-3 and caspase-7mRNA or protein in the cultured cell in the absence of the candidate modulator agent.

11. The method according to claim 1, wherein the identification of said candidate modulator agent to stimulate cell death in a GDNF dependent cell culture system is further confirmed by the detection of the presence of activity of caspase-2 and caspase-7 and the absence of activity of Bax, caspase-3, caspase-8, and caspase-9.

* * * * *